(12) United States Patent
Abdelgany

(10) Patent No.: US 7,194,934 B2
(45) Date of Patent: Mar. 27, 2007

(54) RATCHETING TORQUE WRENCH

(75) Inventor: Mahmoud F. Abdelgany, Rockaway, NJ (US)

(73) Assignee: Custom Spine, Inc., Parsippany, NJ (US)

(*) Notice: Subject to any disclaimer, the term of this patent is extended or adjusted under 35 U.S.C. 154(b) by 0 days.

(21) Appl. No.: 11/280,007

(22) Filed: Nov. 16, 2005

(65) Prior Publication Data

US 2006/0260440 A1 Nov. 23, 2006

Related U.S. Application Data

(60) Provisional application No. 60/683,746, filed on May 23, 2005.

(51) Int. Cl.
*B25B 13/46* (2006.01)

(52) U.S. Cl. .......................... 81/60; 81/63.1; 192/43.1; 408/120

(58) Field of Classification Search ............. 81/54, 81/57, 39, 60–63.2, 112–114, 57.11, 52, 57.12, 81/57.13, 57.14, 318–325; 192/43.2, 184, 192/43
See application file for complete search history.

(56) References Cited

U.S. PATENT DOCUMENTS

| 4,149,820 A | * | 4/1979 | Newlin | 408/120 |
| 4,696,208 A | * | 9/1987 | Lay | 81/58 |
| 5,586,475 A | * | 12/1996 | Wenner | 81/60 |
| 5,609,078 A | * | 3/1997 | Yang | 81/63.1 |
| 5,740,704 A | * | 4/1998 | Payne | 81/60 |
| 5,749,272 A | * | 5/1998 | Phan | 81/62 |

\* cited by examiner

*Primary Examiner*—Lee D. Wilson
*Assistant Examiner*—Anthony Ojini
(74) *Attorney, Agent, or Firm*—Gibb LP. Law Firm, LLC; Mohammad S. Rahman, Esq

(57) ABSTRACT

A ratcheting torque wrench comprising a torsional shaft connected to a hex tip; a sleeve that fits over the torsional shaft; a sleeve dial having a hole and configured to fit around the sleeve such that the diameter of the sleeve dial hole accommodates the sleeve; a shaft dial connected to the sleeve dial; a nylon ring connected to a ratchet housing; a ratchet gear connected to the ratchet housing, the ratchet housing mating with the ratchet gear; a spring connected to the nylon ring and the ratchet gear; a ratchet cover that fits over the ratchet housing; a retaining ring connected to the ratchet cover and configured to engage the torsional shaft; a ratchet fitting connected to the ratchet housing, wherein the ratchet fitting accommodates a first handle, wherein the sleeve has a hole to accommodate a second handle.

16 Claims, 25 Drawing Sheets

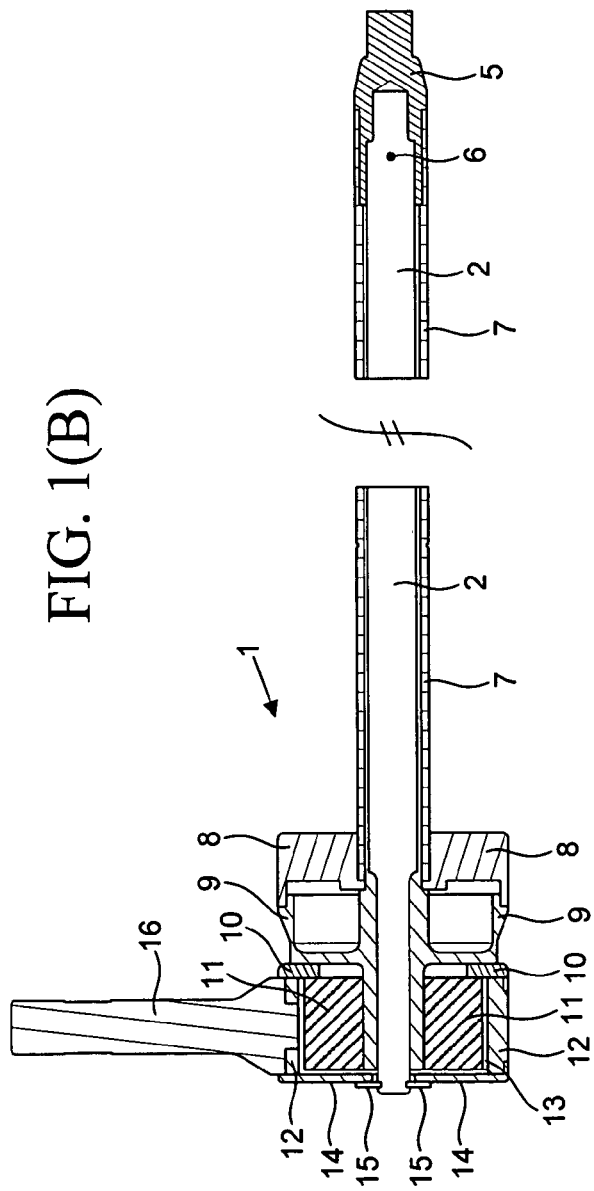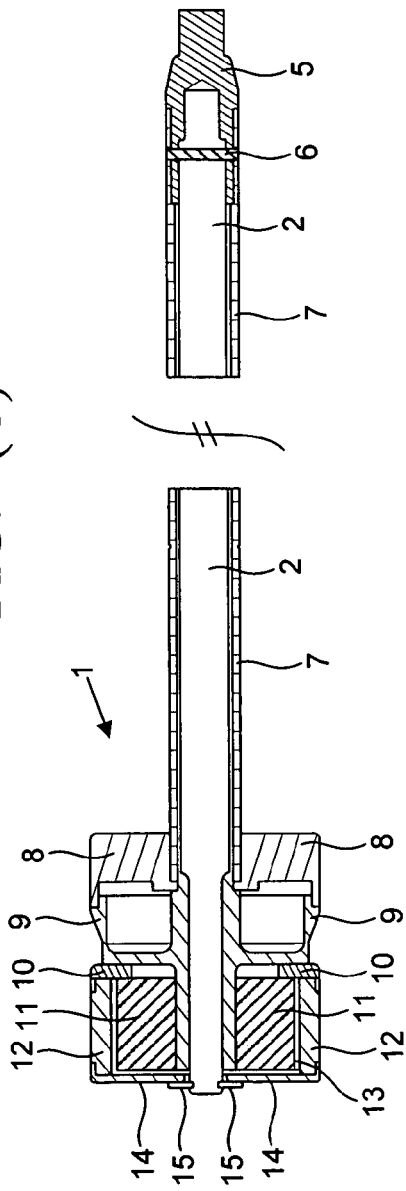
FIG. 1(B)
FIG. 1(C)

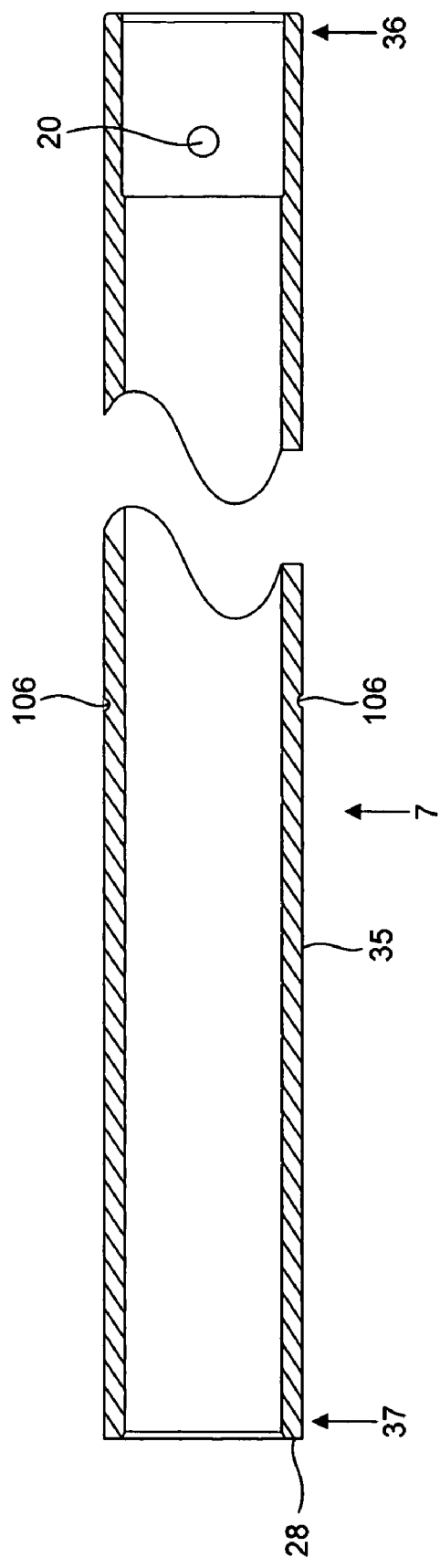

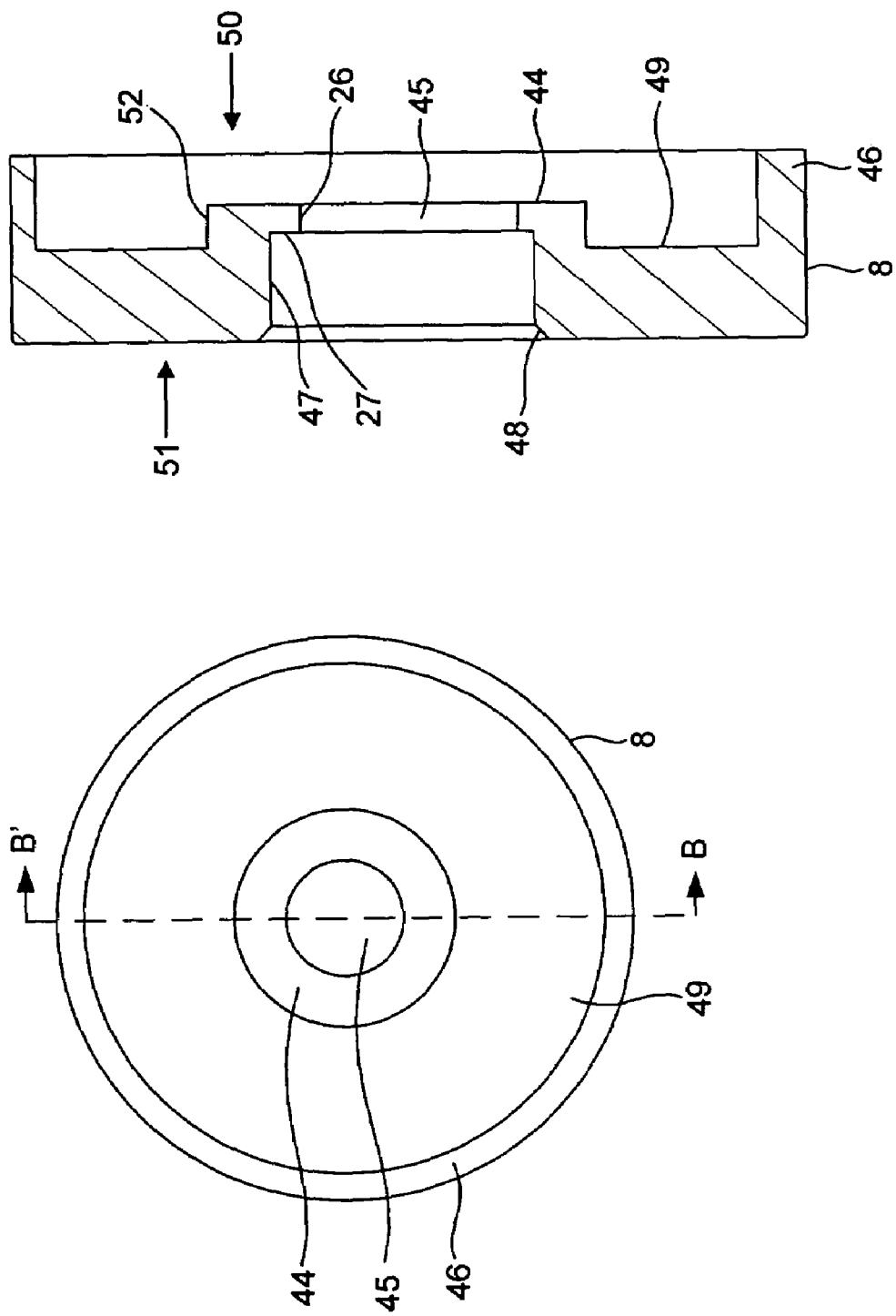

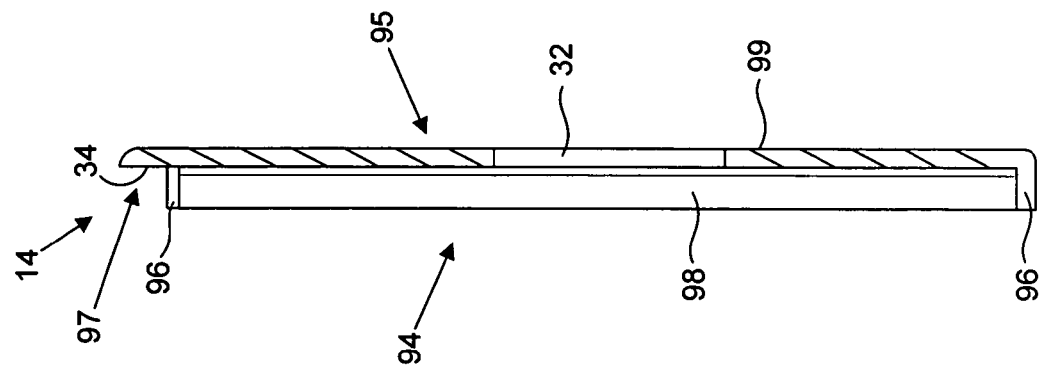
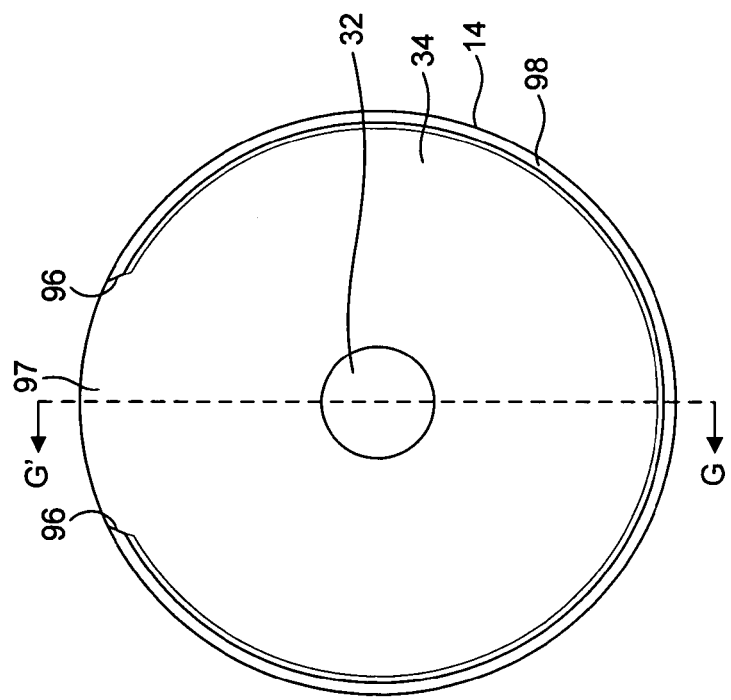
FIG. 11(B)
FIG. 11(A)

RATCHETING TORQUE WRENCH

CROSS-REFERENCE TO RELATED APPLICATION

This application claims the benefit of U.S. Provisional Patent Application No. 60/683,746 filed on May 23, 2005, the contents of which, in its entirety, is herein incorporated by reference.

BACKGROUND

1. Field of the Invention

The embodiments herein generally relate to medical devices, and, more particularly, to medical devices used for spinal surgeries.

2. Description of the Related Art

Most conventional torque wrenches typically have a hex tip at the bottom and a T-handle at the other end of the instrument. Because the orientation of the hex is generally always random, the surgeon rarely gets the optimal handle alignment to apply the needed torque to safely conduct the final tightening of the spinal construct. Most conventional torque wrenches have shortcomings such as: (1) a break away design that allows for a violent sudden motion in order to function, which effects the calibration after multiple usages; (2) limited leverage requires a two-handed operation that leads to having an assistant applying counter-torque force using a counter-torque instrument; (3) too bulky therefore limiting surgeon visibility; and (4) random orientation leading to less than optimal ergonomics for torque application. Therefore, there remains a need for a novel torque wrench where the optimal alignment is generally always guaranteed and which generally overcomes the limitations of the conventional torque wrenches.

SUMMARY

In view of the foregoing, an embodiment herein provides a ratcheting torque wrench comprising a torsional shaft having a first end and a second end distally located from the first end; a hex tip; a dowel pin dimensioned and configured to connect the torsional hex tip to the first end of the torsional shaft; a sleeve dimensioned and configured to fit over the torsional shaft; a sleeve dial having a centrally located hole, wherein the sleeve dial is dimensioned and configured to fit around the sleeve such that the diameter of the sleeve dial hole is dimensioned and configured to accommodate the sleeve; a shaft dial connected to the sleeve dial; a ratchet housing; a nylon ring connected to the ratchet housing; a ratchet gear connected to the ratchet housing, wherein the ratchet gear comprises teeth dimensioned and configured around an outer perimeter of the ratchet gear, and wherein the ratchet housing is dimensioned and configured to mate with the teeth of the ratchet gear, wherein the ratchet housing comprises a hole located through a wall of the ratchet housing; a spring connected to the ratchet housing and the ratchet gear; a ratchet cover dimensioned and configured to fit over the ratchet housing; a retaining ring connected to the ratchet cover and dimensioned and configured to engage the second end of the torsional shaft; a ratchet fitting connected to the hole of the ratchet housing, wherein the ratchet fitting is dimensioned and configured to accommodate a first handle, and wherein the sleeve comprises a hole to accommodate a second handle.

Another embodiment provides an assembly for tightening a locking element in an orthopedic implant, wherein the assembly comprises a torque wrench; a counter-torque wrench operatively connected to the torque wrench; and a ratcheting mechanism operatively connected to the torque wrench. Preferably, the ratcheting mechanism comprises a torsional shaft having a first end and a second end distally located from the first end; a hex tip operatively connected to the torsional shaft; a dowel pin dimensioned and configured to connect the hex tip to the first end of the torsional shaft; a sleeve dimensioned and configured to fit over the torsional shaft; a sleeve dial having a centrally located hole, wherein the sleeve dial is dimensioned and configured to fit around the sleeve such that the diameter of the sleeve dial hole is dimensioned and configured to accommodate the sleeve; a shaft dial connected to the sleeve dial; a ratchet housing positioned around the shaft; a nylon ring connected to the ratchet housing; a ratchet gear connected to the ratchet housing, wherein the ratchet gear comprises teeth dimensioned and configured around an outer perimeter of the ratchet gear, wherein the ratchet housing is dimensioned and configured to mate with the teeth of the ratchet gear, wherein the ratchet housing comprises a hole located through a wall of the ratchet housing; a shim connected to the ratchet housing and the ratchet gear; a retaining ring connected to the ratchet cover and dimensioned and configured to engage the second end of the torsional shaft; a ratchet fitting connected to the hole of the ratchet housing; and a ratchet cover dimensioned and configured to fit over the ratchet housing. Moreover, the ratchet fitting is preferably dimensioned and configured to accommodate a first handle. Furthermore, the sleeve preferably has a hole to accommodate a second handle.

These and other aspects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF THE DRAWINGS

The embodiments herein will be better understood from the following detailed description with reference to the drawings, in which:

FIGS. 1(B) and 1(C) illustrate cross-sectional schematic diagrams of the ratcheting torque wrench of FIG. 1(A) according to an embodiment herein;

FIGS. 3(A) and 3(B) illustrate schematic diagrams of the torque wrench sleeve of the ratcheting torque wrench of FIG. 1(A) according to an embodiment herein;

FIGS. 5(A) and 5(B) illustrate schematic diagrams of the torque wrench sleeve dial of the ratcheting torque wrench of FIG. 1(A) according to an embodiment herein;

FIGS. 11(A) and 11(B) illustrate schematic diagrams of the torque wrench ratchet cover of the ratcheting torque wrench of FIG. 1(A) according to an embodiment herein;

DETAILED DESCRIPTION OF PREFERRED EMBODIMENTS

Figure 1A:
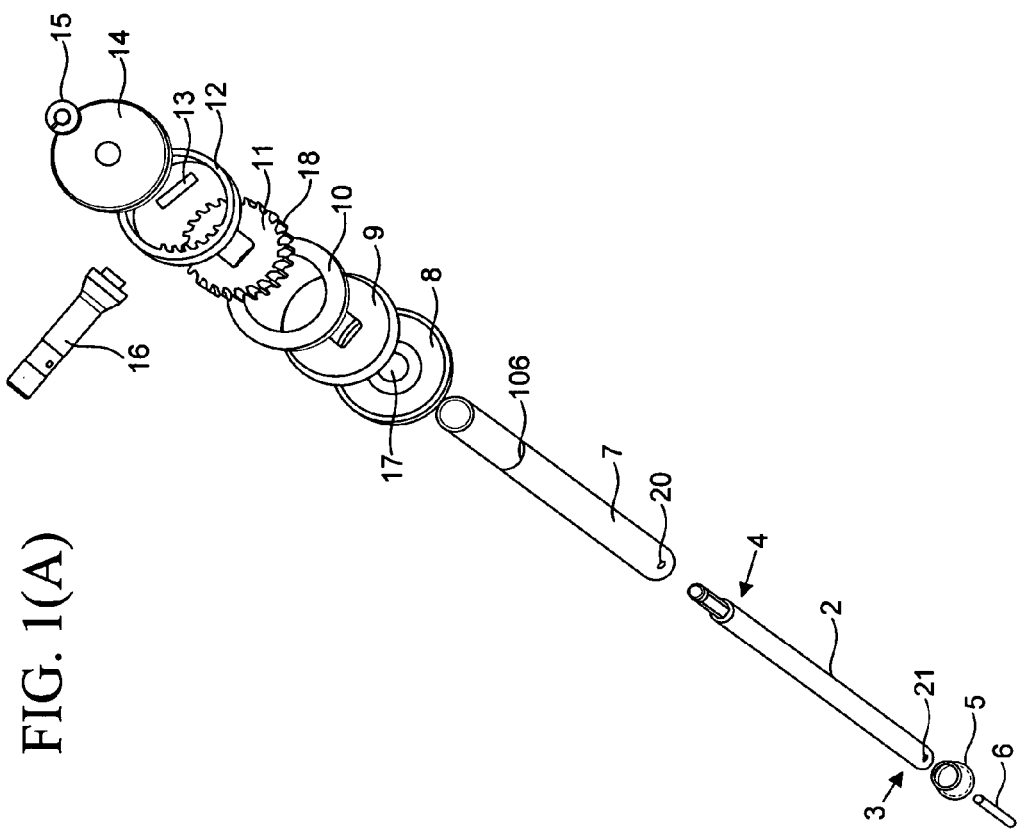
FIG. 1(A) illustrates an exploded view of a ratcheting torque wrench according to an embodiment herein.

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

As mentioned, there remains a need for a novel torque wrench where the optimal alignment is always guaranteed and which generally overcomes the limitations of the conventional torque wrenches. The embodiments herein achieve this by providing a ratcheting torque wrench that provides optimal ergonomically alignment for torque applications during spine surgery. The torque wrench allows one operator to properly perform the final locking step without assistance from another operator every time it is used. This is accomplished due to the ratcheting feature at the top of the instrument. Referring now to the drawings, and more particularly to FIGS. 1(A) through 18, there are shown preferred embodiments.

FIGS. 1(A) through 1(C) illustrate a ratcheting torque wrench 1 and its various components according to an embodiment herein. Generally, the ratcheting torque wrench 1 comprises a torsional shaft 2 having a first end 3 and a second end 4 distally located from the first end 3. A hex tip 5 is connected to the first end 3 of the torsional shaft 2 via a dowel pin 6. A sleeve 7 fits over the torsional shaft 2. A sleeve dial 8 having a centrally located hole 17 fits around the sleeve 7 such that the diameter of the sleeve dial hole 17 is dimensioned to accommodate the sleeve 7. A shaft dial 9 connects to the sleeve dial 8 and a nylon ring 10 connects to the shaft dial 9. A ratchet gear 11 connects to the nylon ring 10, wherein the ratchet gear 11 has teeth 18 configured around an outer perimeter of the ratchet gear 11.

A ratchet housing 12 is configured to mate with the teeth 18 of the ratchet gear 11. A spring 13 connects to the nylon ring 10 and the ratchet gear 11. A ratchet cover 14 fits over the ratchet housing 12 and a retaining ring 15 connects to the ratchet cover 14 and engages the second end 4 of the torsional shaft 2. A ratchet fitting 16 connects to a hole 77 located through the wall 78 (shown in FIG. 9(A)) of the ratchet housing 12. Furthermore, each of the sleeve 7 and torsional shaft 2 have a hole 20, 21, respectively, which are co-aligned to accommodate the pin 6 to secure the hex tip 5 to the shaft 2 and sleeve 7. In another embodiment shown in FIG. 16, a screwdriver-like handle 22 may be attached to the sleeve 7, and the ratchet fitting 16 may also be dimensioned and configured to accommodate a screwdriver-like handle 19. The type of screwdriver-like handle 19, 22 that may be used in accordance with the embodiments herein is described in U.S. patent application Ser. No. 11/076,670 filed on Mar. 10, 2005 and entitled, "Screwdriver Handle", the complete disclosure of which, in its entirety, is herein incorporated by reference.

Figure 2A:
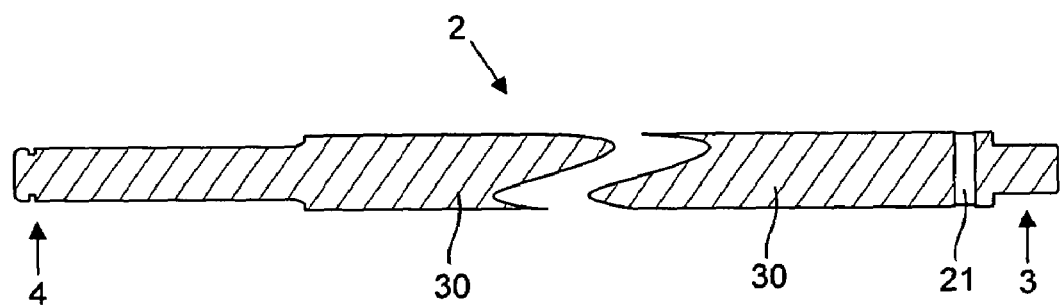
FIG. 2(A) illustrates a cross-sectional schematic diagram of the torque wrench torsional shaft of the ratcheting torque wrench of FIG. 1(A) according to an embodiment herein.
Figure 2B:
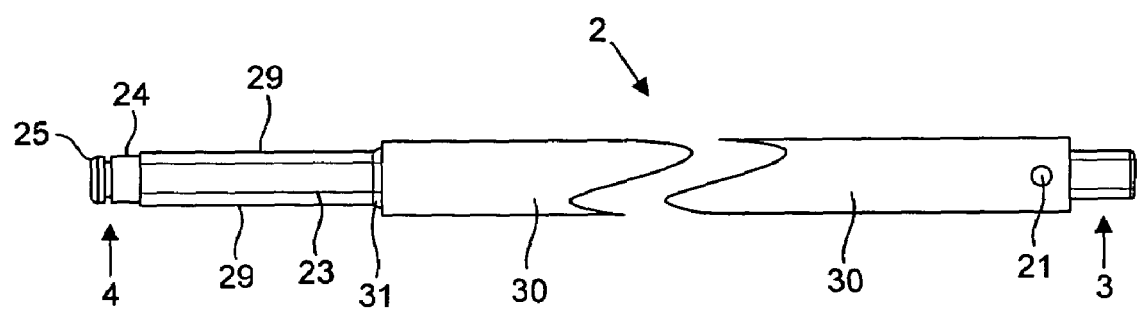
FIG. 2(B) illustrates a schematic diagram of the torque wrench torsional shaft of the ratcheting torque wrench of FIG. 1(A) according to an embodiment herein.

FIGS. 2(A) and 2(B) illustrate the torque wrench torsional shaft 2 of the ratcheting torque wrench 1 of FIG. 1(A). The shaft 2 is preferably in a generally extended cylindrical configuration and includes the first end 3 and second end 4 separated by a middle portion 30. The first end 3 of the shaft 2 is also preferably in a cylindrical configuration having a diameter smaller than the diameter of the middle portion 30 of the shaft 2. The second end 4 of the shaft 4 is preferably has a width smaller than the diameter of the middle portion 30 of the shaft 2. The second end 4 is dimensioned accordingly to accommodate the hole 32 of the ratchet cover 14 (of FIG. 11(A)), wherein the sleeve dial 8 (of FIG. 5(A)) rests on the lip 31 of the shaft 2. The second end 4 includes an elongated base 23 with an intermediate portion 24 positioned on the base 23 and terminating with a raised catch 25.

The intermediate portion 24 and catch 25 are preferably embodied in a cylindrical configuration. The base 23 is preferably embodied in a rectilinear configuration with defined edges 29. Preferably, the width of the base 23 is larger than the diameter of the intermediate portion 24 and catch 25. The hole 21 that accommodates the pin 6 (of FIG. 14(A)) is preferably configured in the middle portion 30 of the shaft 2 and positioned towards the first end 3 of the shaft 2.

FIGS. 3(A) and 3(B) illustrate schematic diagrams of the torque wrench sleeve 7 of the ratcheting torque wrench 1 of FIG. 1(A). The sleeve 7 is preferably in a cylindrical configuration having an outer body 35 and a hollow inner portion 33. The sleeve 7 also has a first end 36 positioned opposite to a second end 37, wherein the hole 20 for accommodating the pin 6 (of FIG. 14(A)) is preferably configured towards the first end 36 of the sleeve 7 such that when the sleeve 7 is positioned over the shaft 2 (of FIG. 2(B)), the respective holes 20, 21 align. Furthermore, the sleeve 7 is preferably dimensioned is allow the shaft 2 to properly fit within the hollow portion 33 of the sleeve. The shaft 2 is dimensioned slightly longer than the sleeve 7, whereby the second end 4 of the shaft 2 extends beyond the second end 37 of the sleeve 7 when the shaft 2 is inserted in the sleeve 7. Preferably, when the sleeve 7 is inserted over the shaft 2, the lip 31 of shaft 2 aligns with the edge 28 of the second end 37 of the sleeve 7. Additionally, the sleeve 7 comprises a groove 106 configured around the outer body 35.

Figure 1D:
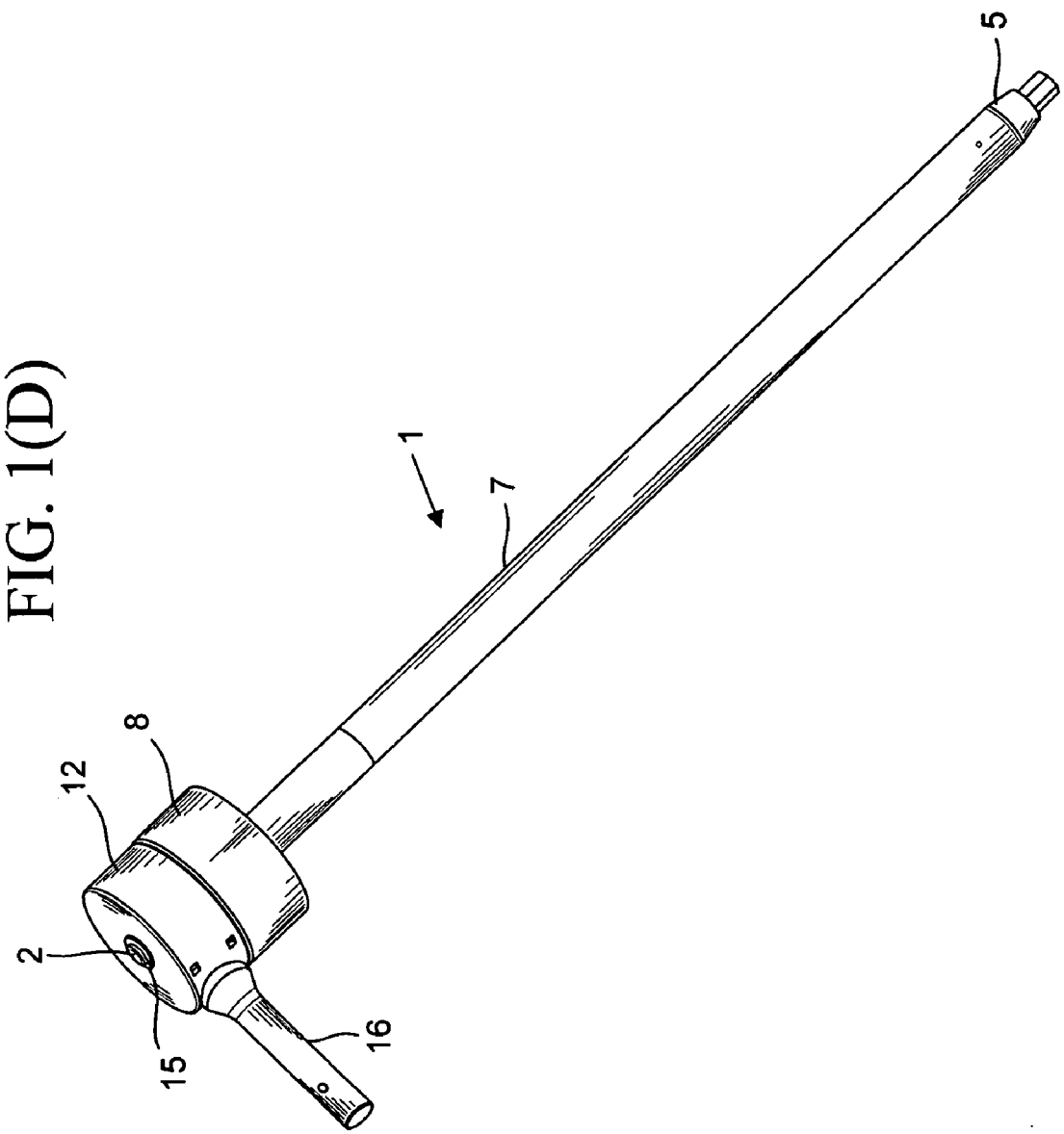
FIG. 1(D) illustrates a schematic diagram of an assembled ratcheting torque wrench according to an embodiment herein.
Figure 4A:
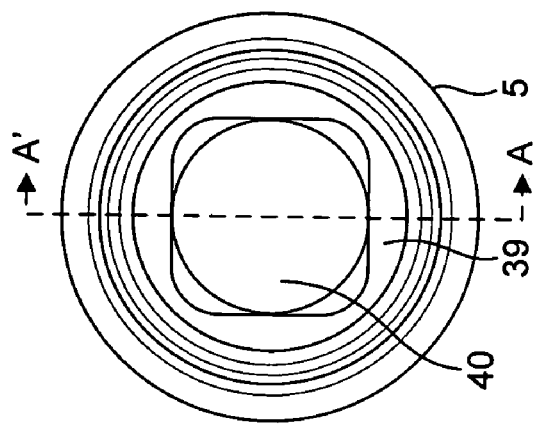
FIGS. 4(A) through 4(C) illustrate schematic diagrams of the torque wrench hex tip of the ratcheting torque wrench of FIG. 1(A) according to an embodiment herein.
Figure 4B:
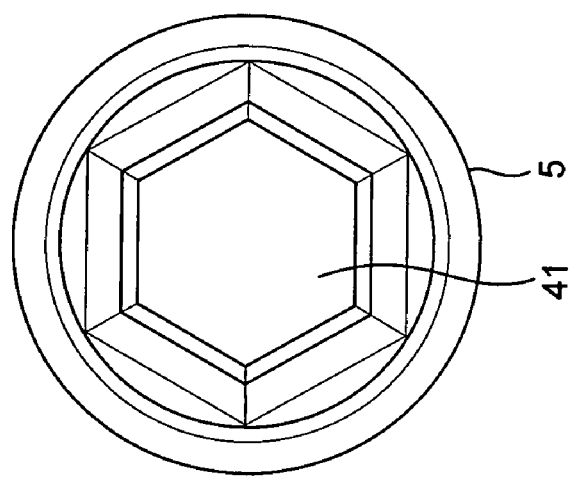
Figure 4C:
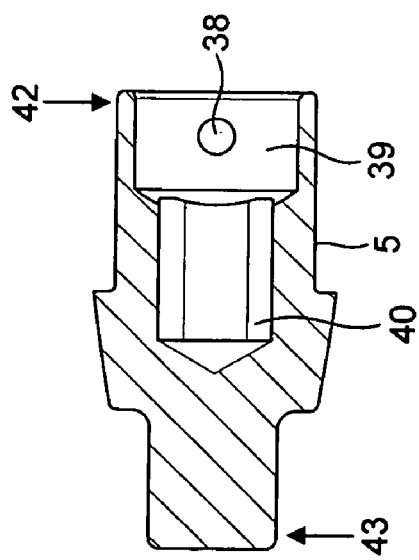

FIGS. 4(A) through 4(C) illustrate schematic diagrams of the torque wrench hex tip 5 of the ratcheting torque wrench 1 of FIG. 1(A), with FIG. 4(A) illustrating the cross-sectional view of the tip 5 cut along line A–A' of FIG. 4(C). The tip 5 comprises a top end 42 positioned opposite to a bottom end 43, wherein a series of holes 39, 40 are configured in the tip 5 beginning from the top end 42. A first hole 39 is configured at a slightly larger diametrical configuration as the middle portion 30 of the shaft 2 (of FIG. 2(B)) and outer body 35 of sleeve 7. Next, a second hole 40 is configured below the first hole 39, whereby the second hole 40 is configured at substantially the same diametrical configuration as the first end 3 of the shaft 2 (of FIG. 2(B)). A pin hole 38 is configured through the top end 42 of the tip 5, whereby the pin hole 38 is dimensioned to accommodate the pin 6 (of FIG. 14(A)). The bottom end 43 preferably terminates with a hex configuration 41 to accommodate a hex screwdriver device. With further reference to FIG. 1, in assembly, the first end 3 of the shaft 2 is inserted in the second hole 40 of the hex tip 5. As this occurs, a part of the middle portion 30 of the shaft 2 fits into the first hole 39 of the hex tip 5 with the hole 21 of the shaft 2 aligning with the pin hole 38 of the hex tip 5. Then, the sleeve 7 is inserted over the shaft 2 with a portion of the first end 36 of the sleeve 7 being inserted into the first hole 39 of the hex tip 5 with the hole 20 of the sleeve 7 aligning with the hole 21 of the shaft 2 and pin hole 38 of the hex tip 5. Thereafter, pin 6 is inserted into the aligned holes 20, 21, 38 to secure the hex tip 5, sleeve 7, and shaft 2 together.

FIGS. 5(A) and 5(B) illustrate schematic diagrams of the torque wrench sleeve dial 8 of the ratcheting torque wrench 1 of FIG. 1(A) with FIG. 5(B) illustrating the cross-sectional view of the sleeve dial 8 cut along line B–B' of FIG. 5(A). The sleeve dial 8 is preferably configured in a disc-like configuration having a raised outer wall 46 and a centrally located hole 45. The upper side 50 of the sleeve dial 8 comprises a bi-level upper surface having a recessed outer portion 49 and a raised inner portion 44, wherein the raised inner portion 44 immediately surrounds hole 45. Moreover, the recessed outer portion 49 is bounded by the outer wall 46 on one side and the raised platform 52 on the other side, wherein the raised platform 52 defines the raised inner portion 44. The diameter of the hole 45 preferably becomes larger towards the bottom side 51 of the sleeve dial 8. The hole 45 has a first diameter defined by wall 26, a second larger diameter defined by wall 47, and finally a third largest diameter defined by tapered wall 48. With reference to FIGS. 1(A) through 3(B), in assembly, the second end 4 of the shaft 2 that extends out of the second end 37 of sleeve 7 fits through hole 45 of the sleeve dial 8 whereby the lip 31 of the shaft 2 rests against the end portion 27 of wall 47 of hole 45 of the sleeve dial 8. Thus, the sleeve dial 8 is prevented from moving past lip 31 of the shaft 2.

Figure 6A:
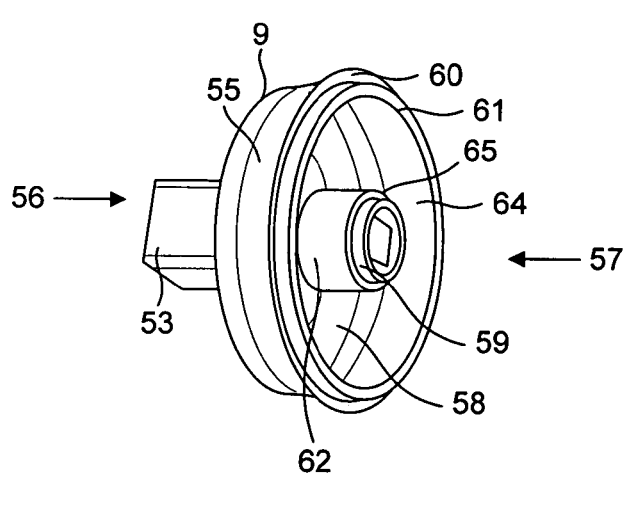
FIGS. 6(A) through 6(C) illustrate schematic diagrams of the torque wrench shaft dial of the ratcheting torque wrench of FIG. 1(A) according to an embodiment herein.
Figure 6C:
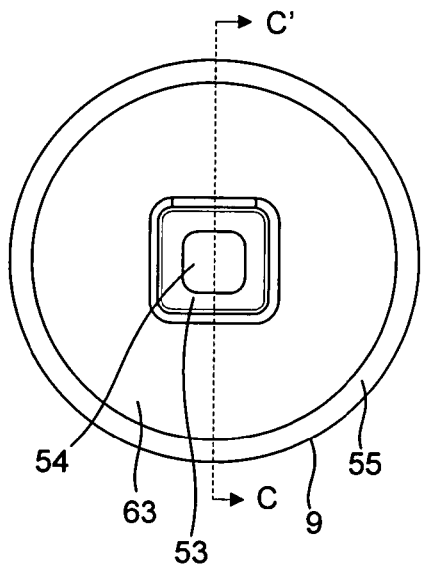
Figure 6B:
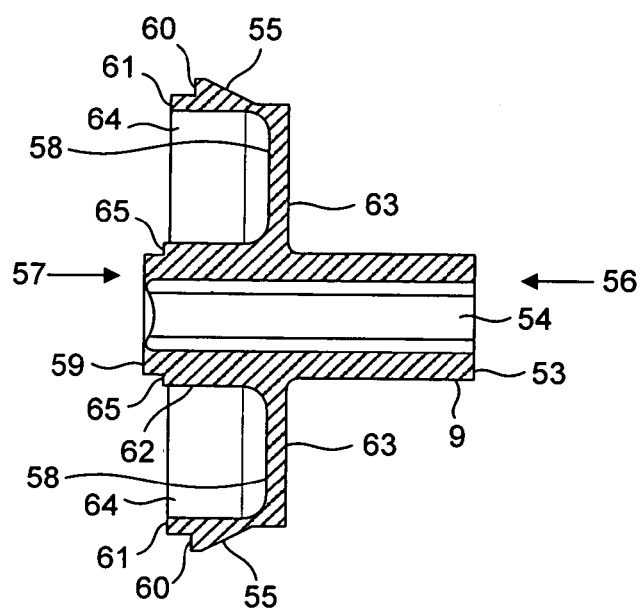

FIGS. 6(A) through 6(C) illustrate schematic diagrams of the torque wrench shaft dial 9 of the ratcheting torque wrench 1 of FIG. 1(A) with FIG. 6(B) illustrating the cross-sectional view of the shaft dial 9 cut along line C–C' of FIG. 6(C). The shaft dial 9, which is generally configured in a cylindrical shape, comprises a top side 56 and a bottom side 57. A top view of the top side 56 is illustrated in FIG. 6(C). The top side 56 comprises an upper disc surface 63 with a rectilinear block 53 having a hollow inner portion 54 configured in the center of the upper disc surface. Positioned below the upper disc surface 63 is a sloping boundary wall 55 having an outer diameter larger than the outer diameter of the upper disc surface 63. On the underside of the sloping boundary wall 55 is a lip 60 having a thickness equal to the difference between the diameter of the sloping boundary wall 55 and the upper disc surface 63. The lip 60 faces the bottom side 57 of the shaft dial 9, wherein the bottom side 57 comprises a cup-like configuration having an outer wall 61 and a generally hollowed inner bowl 64 terminating with a bottom surface 58. Configured in the center of the inner bowl 64 is a generally cylindrical boss 62 terminating with a protruding, generally cylindrical, tip 59. Preferably, the boss 62 is diametrically larger and is longer than the tip 59. The outer wall 61 projects from the lip 60 and is slightly recessed with respect to the lip 60 such that the outer diameter of the lip 60 extends further than the outer diameter of the outer wall 61. With reference to FIGS. 1(A) through 5(B), in assembly, the second end 4 of the shaft 2 fits through the hollow portion 54 of the boss 62 and extends out through the block 53 of the shaft dial 9. The shape of the hollow portion 54 is substantially similar to the shape of the base 23 of the shaft 2. Furthermore, when the shaft dial 9 is inserted over the second end 4 of the shaft 2 (that has been previously been assembled to the hex tip 5, sleeve 7, and sleeve dial 8), the lip 60 of the shaft dial 9 rests on the outer wall 46 of the sleeve dial 8 with the outer wall 61 of the shaft dial 9 resting against the outer wall 46 of the sleeve dial 8. The tip 59 of the boss 62 of the shaft dial 9 projects through the hole 45 of the sleeve dial 8 such that the tip 59 terminates at the point where the wall 47 of the hole 45 of the sleeve dial 8 begins with the rim 65 of the boss 62 resting against the raised inner portion 44 of the sleeve dial 8.

Figure 7A:
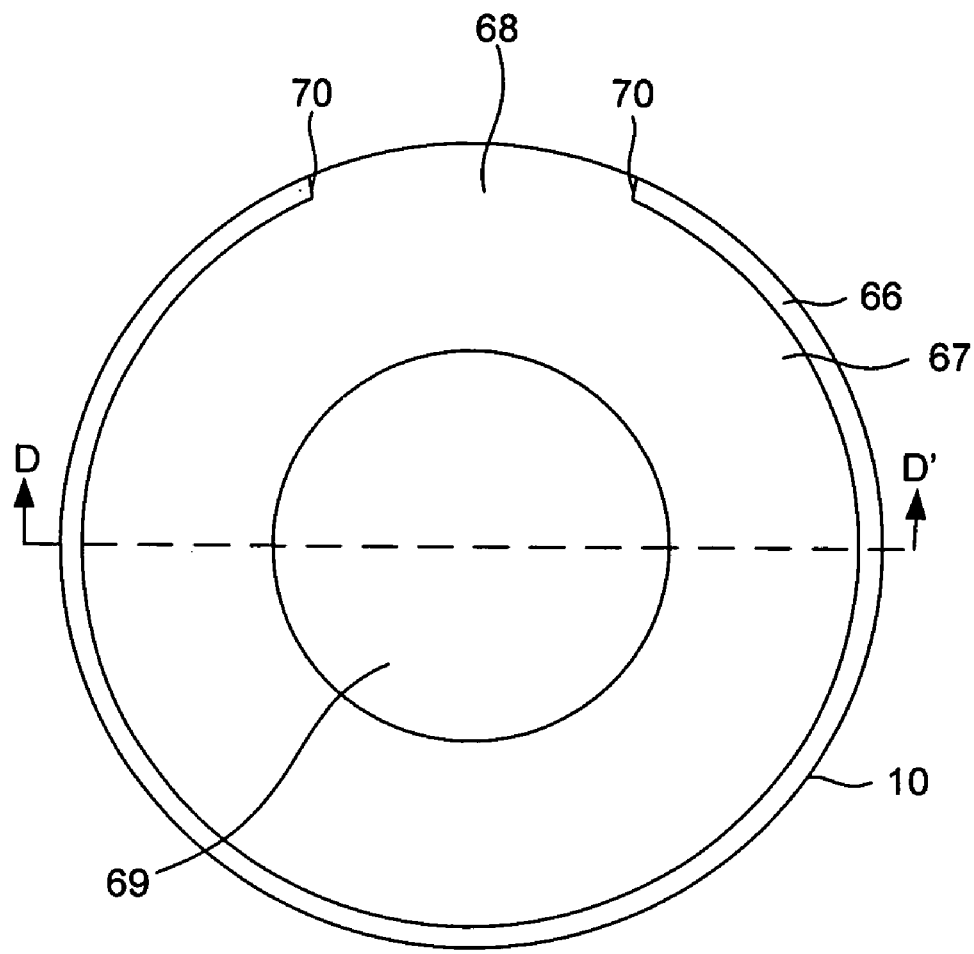
FIGS. 7(A) and 7(B) illustrate schematic diagrams of the torque wrench ring of the ratcheting torque wrench of FIG. 1(A) according to an embodiment herein.
Figure 7B:
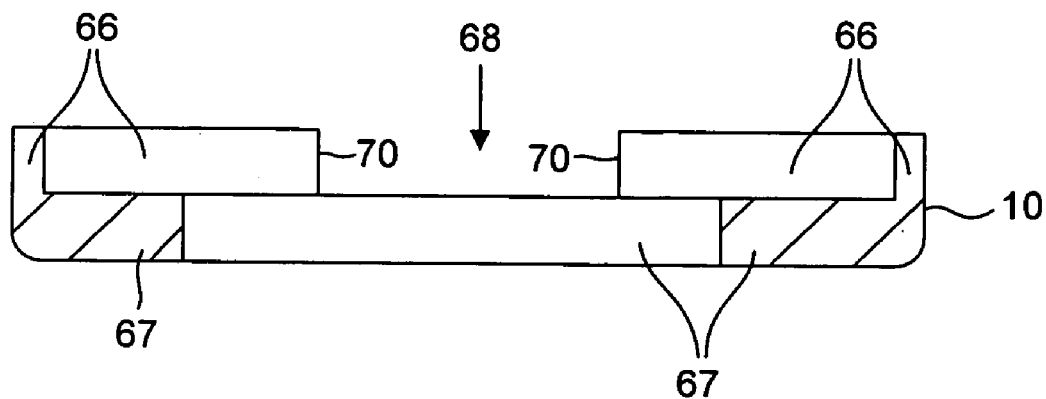

FIGS. 7(A) and 7(B) illustrate schematic diagrams of the torque wrench ring 10 of the ratcheting torque wrench 1 of FIG. 1(A) with FIG. 7(B) illustrating the cross-sectional view of the ring 10 cut along line D–D' of FIG. 7(A). The ring 10, which preferably comprises nylon, comprises a disc portion 67 with a raised outer wall 66 configured along the rim of the disc portion 67. The raised outer wall 66 does not encircle the totality of the circumference of the disc portion 67 of the ring 10, but instead a gap 68 is present between the ends 70 of the raised outer wall 66. Preferably, the inner portion 69 of the ring 10 is hollow. With reference to FIGS. 1(A) through 6(C), in assembly, the ring 10 is positioned on the upper disc surface 63 of the shaft dial 9 such that the block 53 of the shaft dial 9 projects through the hollow inner portion 69 of the ring 10.

Figure 8A:
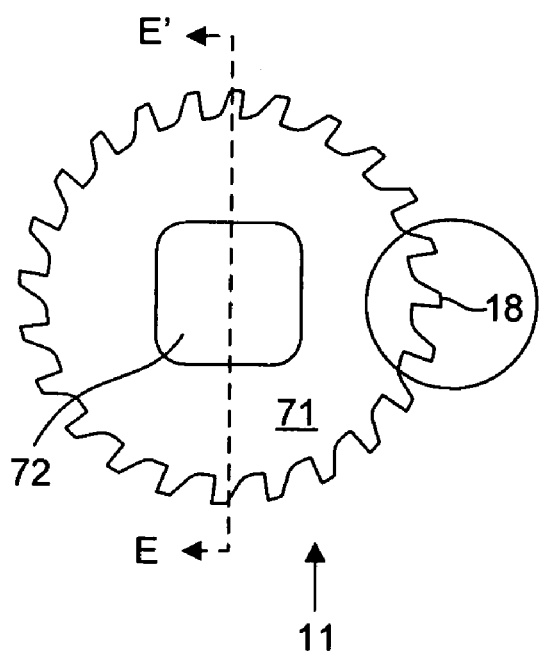
FIGS. 8(A) through 8(C) illustrate schematic diagrams of the torque wrench ratchet gear of the ratcheting torque wrench of FIG. 1(A) according to an embodiment herein.
Figure 8B:
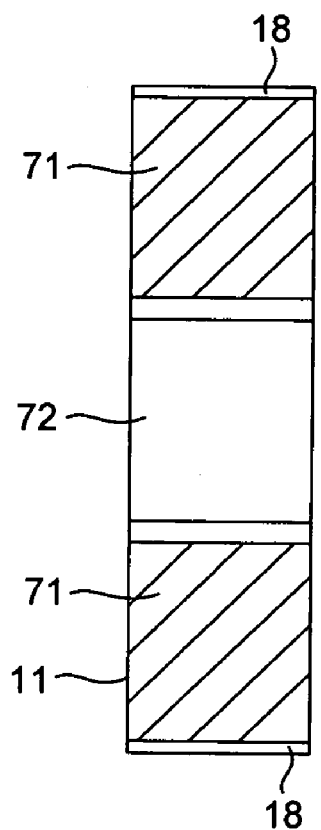
Figure 8C:
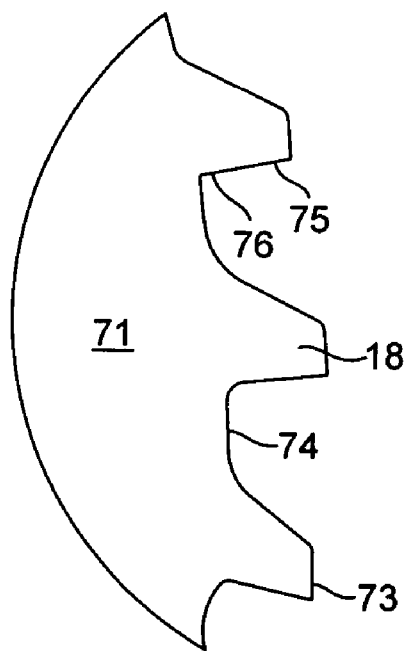

FIGS. 8(A) through 8(C) illustrate schematic diagrams of the torque wrench ratchet gear 11 of the ratcheting torque wrench 1 of FIG. 1(A) with FIG. 8(B) illustrating the cross-sectional view of the gear 11 cut along line E–E' of FIG. 8(A) and with FIG. 8(C) illustrating an enlarged isolated view of the encircled area of FIG. 8(A). The gear 11 is generally configured in a disc-like shape and comprises a center 72 and a body portion 71, wherein the body portion 71 has an outer periphery of teeth 18 configured with any suitable dimensions for its top land 73, bottom land 74, face 75, and flank 76. With reference to FIGS. 6(A) through 7(B), the center 72 of the gear 11 is preferably hollow and is configured to securely fit around block 53 of the shaft dial 9, wherein the gear 11 is placed over the ring 10 with the block 53 of the shaft dial 9 positioned through the hollow center 72 of the gear 11 such that thickness of the ring 10 separates the upper disc surface 63 of the shaft dial 9 from the gear 11.

Figure 9A:
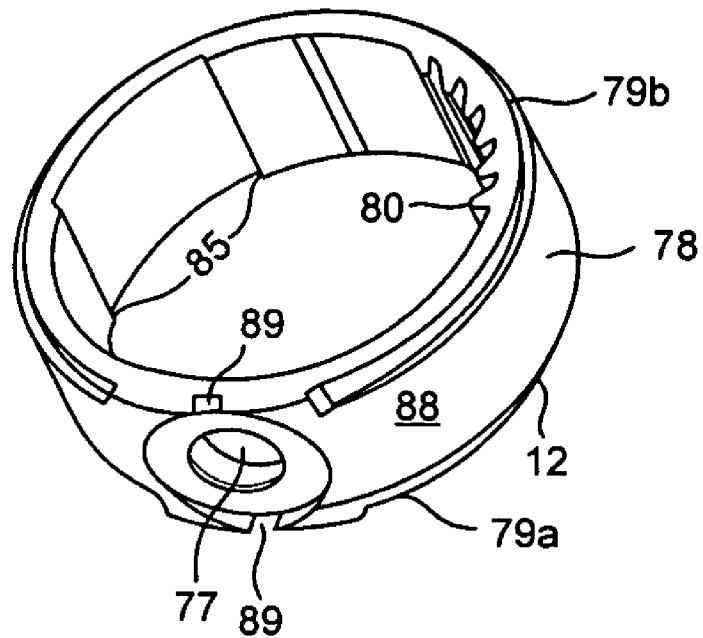
FIGS. 9(A) through 9(F) illustrate schematic diagrams of the torque wrench ratchet housing of the ratcheting torque wrench of FIG. 1(A) according to an embodiment herein.
Figure 9B:
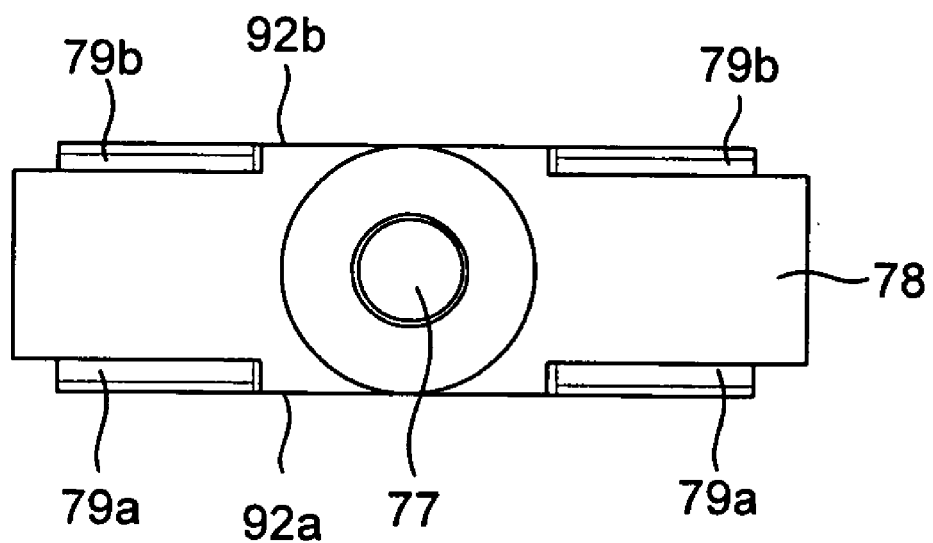
Figure 9C:
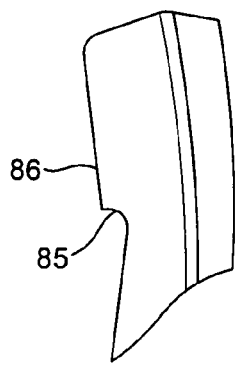
Figure 9F:
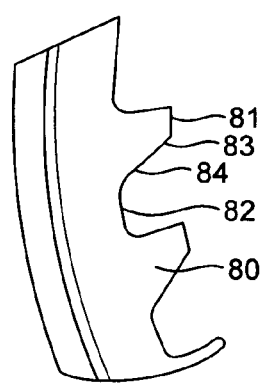
Figure 9E:
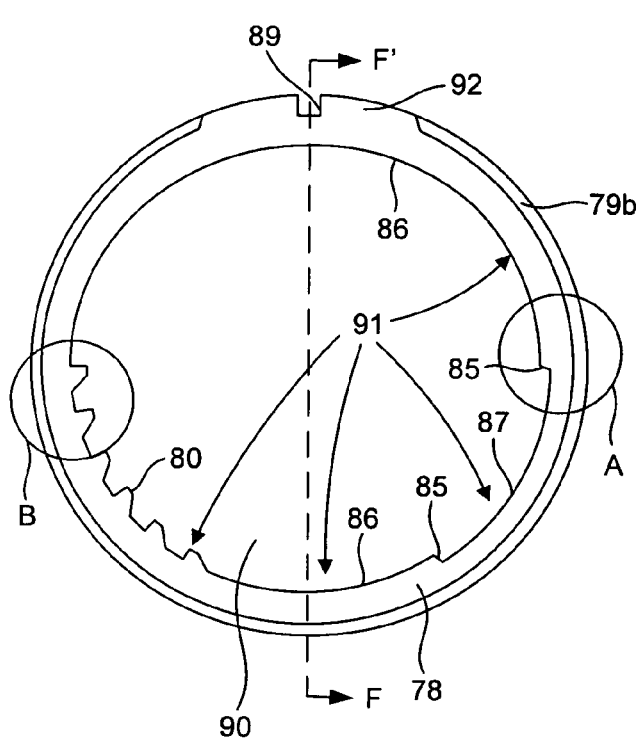
Figure 9D:
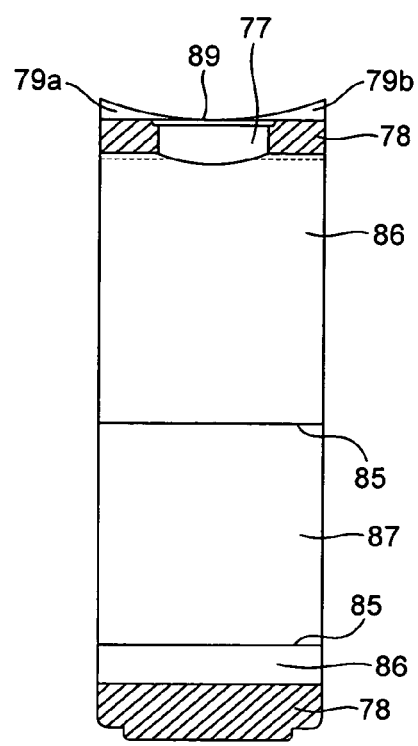

FIGS. 9(A) through 9(F) illustrate schematic diagrams of the torque wrench ratchet housing 12 of the ratcheting torque wrench 1 of FIG. 1(A) with FIG. 9(D) illustrating the cross-sectional view of the ratchet housing 12 cut along line F–F' of FIG. 9(E), with FIG. 9(C) illustrating an enlarged isolated view of the encircled area 'A' of FIG. 9(E), and with FIG. 9(F) illustrating an enlarged isolated view of the encircled area 'B' of FIG. 9(E). The ratchet housing 12 is preferably configured in a ring-like configuration having a body portion 78 and a hollow center portion 90. The body portion 78 comprises a generally smooth outer surface 88 and an inner surface 91 having a plurality of portions including a generally smooth portion 86, a gear-engaging portion 80, and a recessed portion 87. The recessed portion 87 is recessed with respect to the smooth portion 86 through the addition of a plurality of notches 85 that separate the smooth portion 86 from the recessed portion 87. The gear-engaging portion 80 is configured to mate with the teeth 18 of the gear 11 (of FIG. 8(A)). Moreover, the gear-engaging portion 80 may be configured with any suitable dimensions typical for its top land 81, bottom land 82, face 83, and flank 84. The body portion 78 of the ratchet housing 12 also includes hole 77. Furthermore, the body portion 78 includes a partially recessed upper edge 79b and lower edge 79a around the periphery of the body portion 78 except the area above 92b and the area below 92a where the hole 77 is configured. Moreover, the body portion 78 includes a groove 89 the area above 92b and the area below 92a the hole 77 in the body portion 78. With reference to FIGS. 7(A) through 8(C), in assembly, gear 11 fits in the hollow center portion 90 of the ratchet housing 12, and the ratchet housing 12 connects to the ring 10 such that the raised outer wall 66 of the ring 10 fits into the recessed lower edge 79a of the body portion 78 of the ratchet housing 12, wherein the area below 92a the hole 77 fits into gap 68 of the ring 10 to provide a generally secured fitting of the ratchet housing 12 to the ring 10.

Figure 10A:
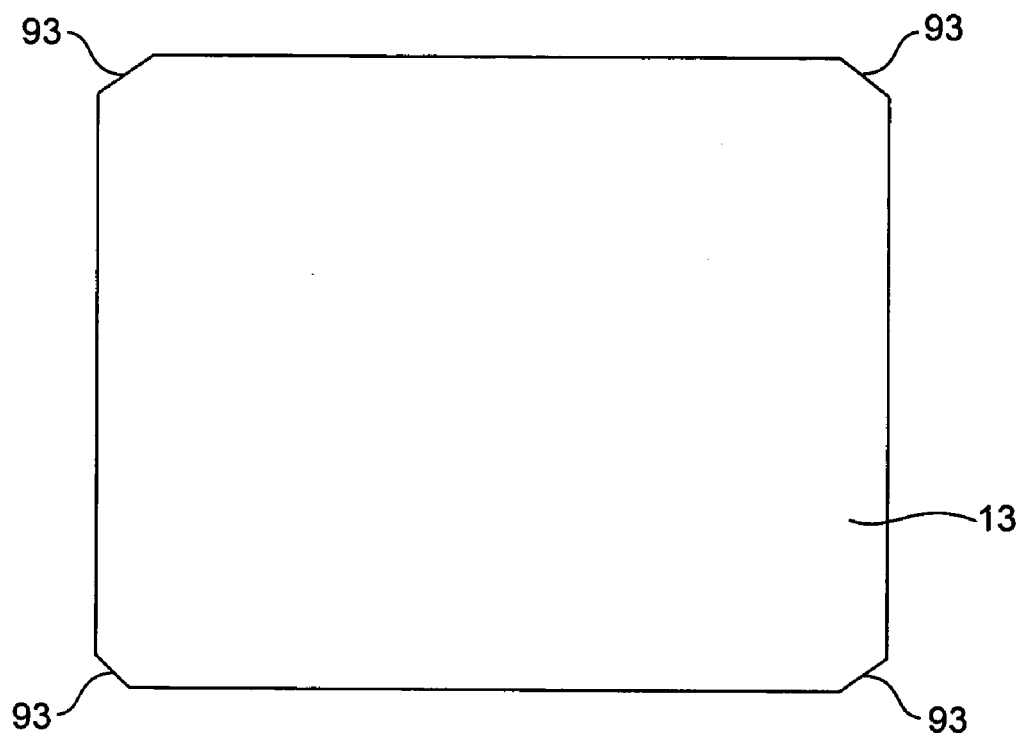
FIGS. 10(A) and 10(B) illustrate schematic diagrams of the torque wrench spring of the ratcheting torque wrench of FIG. 1(A) according to an embodiment herein.
Figure 10B:
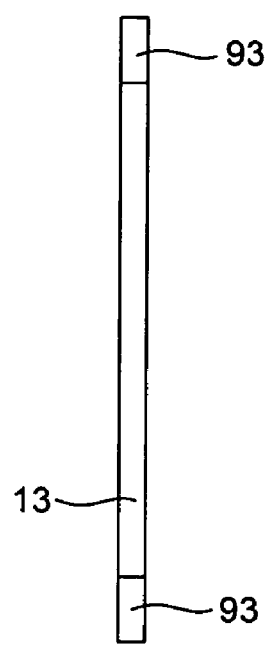

FIGS. 10(A) and 10(B) illustrate schematic diagrams of the torque wrench spring 13 of the ratcheting torque wrench 1 of FIG. 1(A). Preferably, the spring 13 is embodied as a flexible thin stainless steel shim that, in assembly, and with reference to FIGS. 8(A) through 9(B), fits into the recessed portion 87 of the inner surface 91 of the ratchet housing 12, whereby the notches 85 keep the spring 13 in place. Generally, the spring 13 aids in providing wear-protection for the teeth 18 of the gear 11. Moreover, the spring 13 may have beveled corners 93.

FIGS. 11(A) and 11(B) illustrate schematic diagrams of the torque wrench ratchet cover 14 of the ratcheting torque wrench 1 of FIG. 1(A) with FIG. 11(B) illustrating the cross-sectional view of the ratchet cover 14 cut along line G–G' of FIG. 11(A). The ratchet cover 14 is generally configured in a disc-like configuration with a top side 95 and a bottom side 94. The top side 95 comprises a top surface 99. Moreover, the bottom side 94 comprises a bottom surface 34 with a raised outer wall 98 configured along the rim of the bottom surface 34. The raised outer wall 98 does not encircle the totality of the circumference of the bottom surface 34 of the bottom side 94 of the ratchet cover 14, but instead a gap 97 is present between the ends 96 of the raised outer wall 98. Preferably, the inner portion 32 of the ratchet cover 14 is hollow. With reference to FIGS. 1(A) through 10(B), in assembly, the bottom side 94 of the ratchet cover 14 is positioned on the ratchet housing 12 such that the raised outer wall 98 of the ratchet cover 14 fits into the recessed upper edge 79b of the body portion 78 of the ratchet housing 12, wherein the area above 92b the hole 77 of the ratchet housing 12 fits into gap 97 of the ratchet cover 14 to provide a generally secured fitting of the ratchet housing 12 to the ratchet cover 14. Moreover, the block 53 of the shaft dial 9 projects through the hollow inner portion 32 of the ratchet cover 14 to allow the raised catch 25 of the second end 4 of the shaft 2 to also project through the hollow inner portion 32 of the ratchet cover 14 and out through the top side 95 of the ratchet cover 14.

Figure 12:
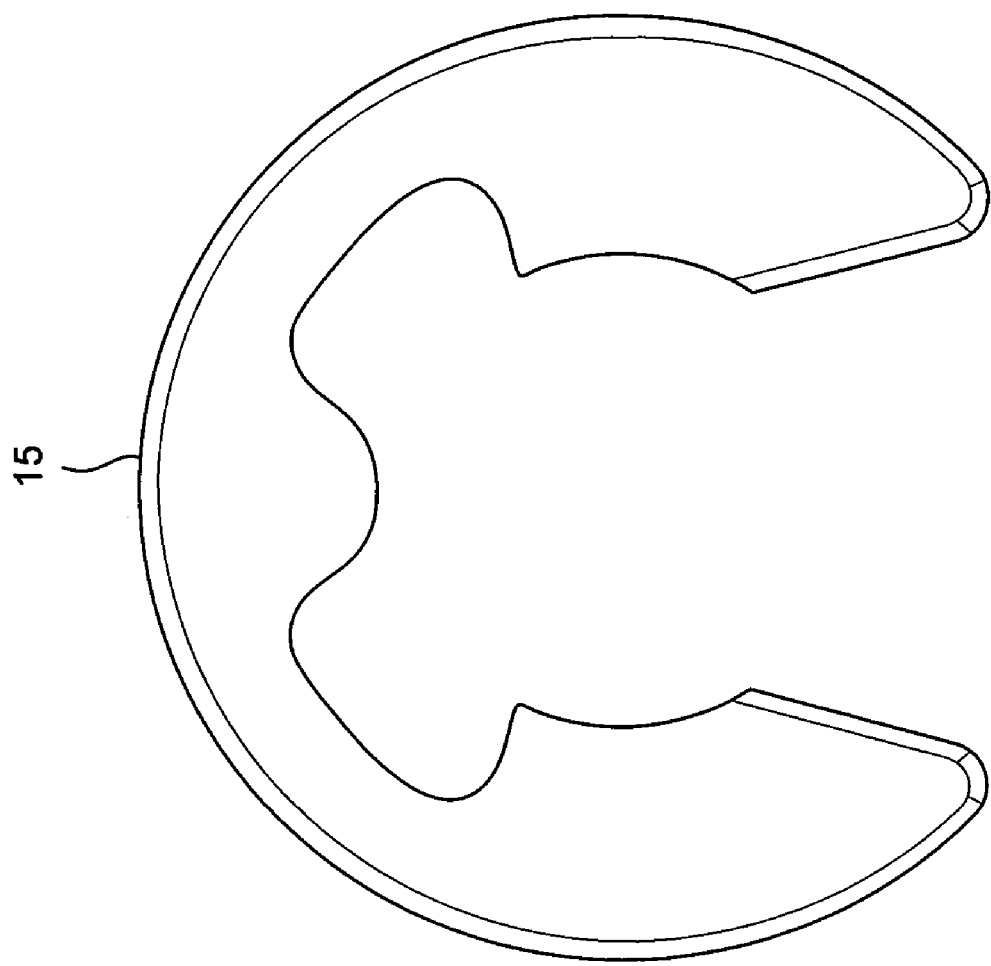
FIG. 12 illustrates a schematic diagram of the torque wrench retaining ring of the ratcheting torque wrench of FIG. 1(A) according to an embodiment herein.

FIG. 12 illustrates a schematic diagram of the torque wrench retaining ring 15 of the ratcheting torque wrench 1 of FIG. 1(A). With further reference to FIGS. 1 through 11(B), in assembly, the retaining ring 15 may be configured in any appropriate configuration to engage the raised catch 25 of the second end 4 of the shaft 2 and to secure the ratchet cover 14 to the shaft 2 as well as the ratchet housing 12, thereby providing a secured fitting of all of the components of the ratcheting torque wrench 1 with respect to one another.

Figure 13A:
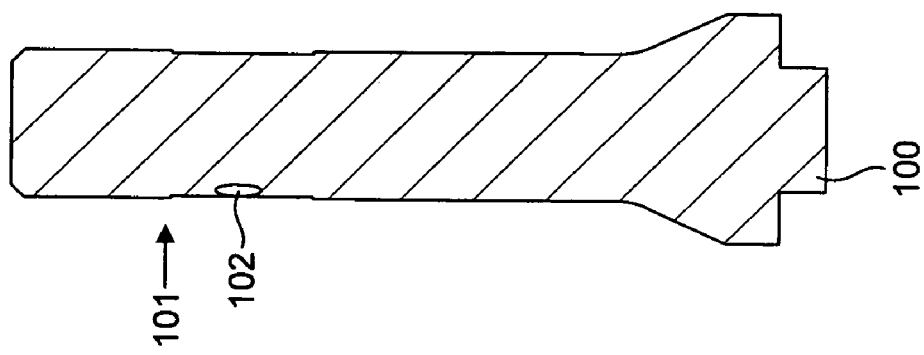
FIGS. 13(A) and 13(B) illustrate schematic diagrams of the torque wrench ratchet fitting of the ratcheting torque wrench of FIG. 1(A) according to an embodiment herein.
Figure 13B:
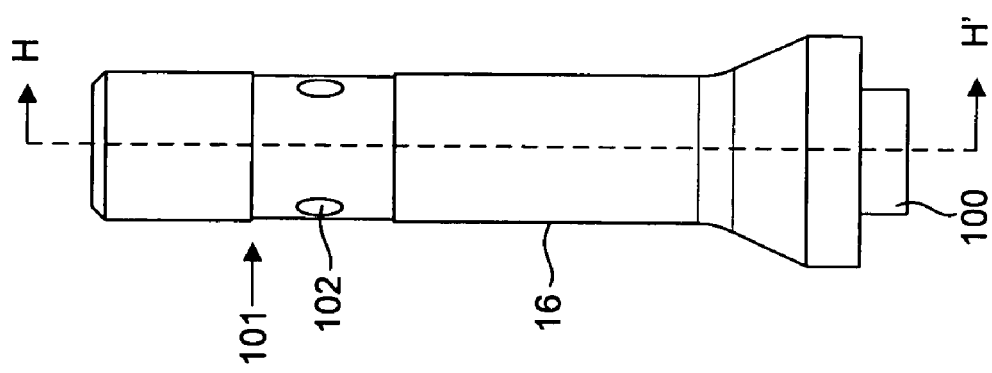

FIGS. 13(A) and 13(B) illustrate schematic diagrams of the torque wrench ratchet fitting 16 of the ratcheting torque wrench 1 of FIG. 1(A) with FIG. 13(B) illustrating the cross-sectional view of the ratchet fitting 16 cut along line H–H' of FIG. 13(A). Generally, the ratchet fitting 16 includes an anchor end 100 positioned opposite to a handle-receiving end 101. With further reference to FIG. 9(A), the anchor end 100 is configured to fit into the hole 77 of the ratchet housing 12 to secure the ratchet fitting 16 to the ratchet housing 12. The handle-receiving end 101 is configured to receive a screwdriver-like handle 19, 22 (of FIG. 16), and wherein the handle-receiving end 101 comprises a connecting mechanism 102, which may connect to the type of handle described in U.S. patent application Ser. No. 11/076,670 filed on Mar. 10, 2005 and entitled, "Screwdriver Handle", the complete disclosure of which, in its entirety, is herein incorporated by reference.

Figure 14A:
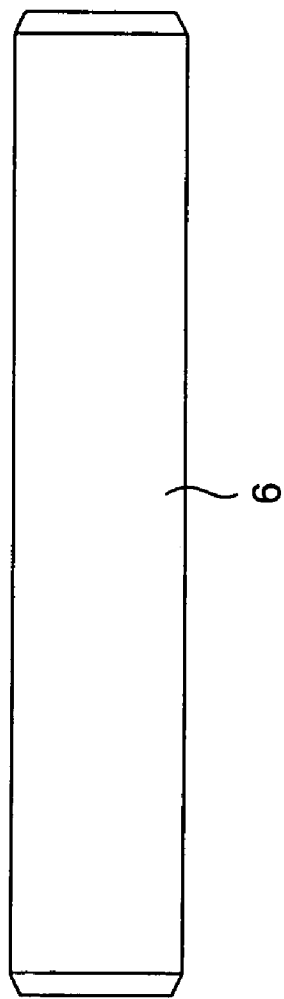
FIGS. 14(A) and 14(B) illustrate schematic diagrams of the torque wrench pin of the ratcheting torque wrench of FIG. 1(A) according to an embodiment herein.
Figure 14B:
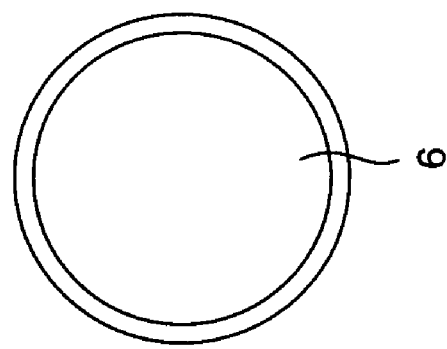

FIGS. 14(A) and 14(B) illustrate schematic diagrams of the torque wrench pin 6 of the ratcheting torque wrench 1 of FIG. 1(A), whereby the pin 6 is preferably embodied as a dowel pin, and as previously described, and with further reference to FIGS. 1(A) through 4(C), secures the hex tip 5 to the shaft 2 and sleeve 7 by fitting into respective holes 38, 21, 20.

Figure 15A:
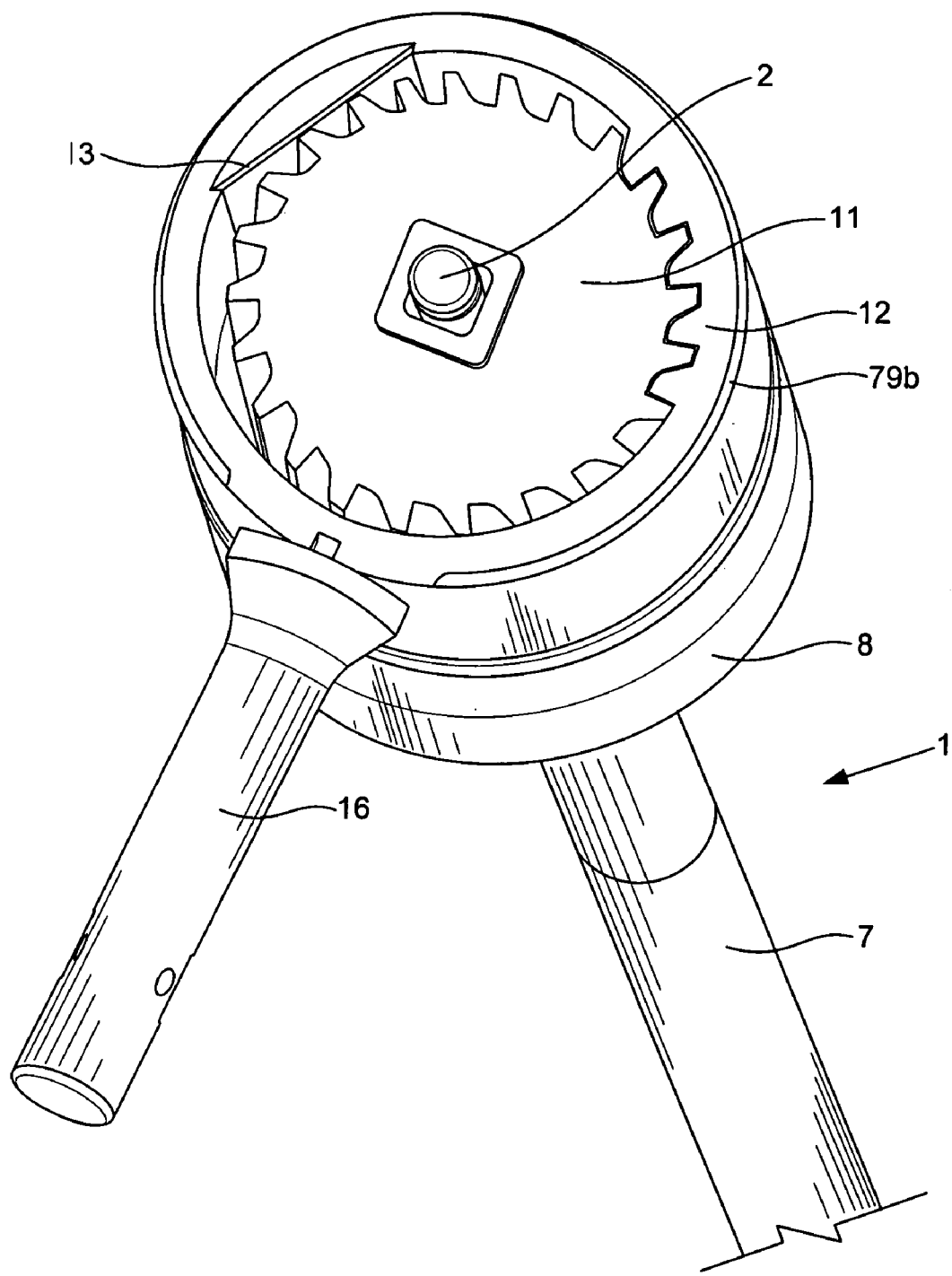
FIG. 15(A) illustrates a schematic diagram of an assembled ratcheting torque wrench with the ratchet cover and retaining ring removed according to an embodiment herein.
Figure 15B:
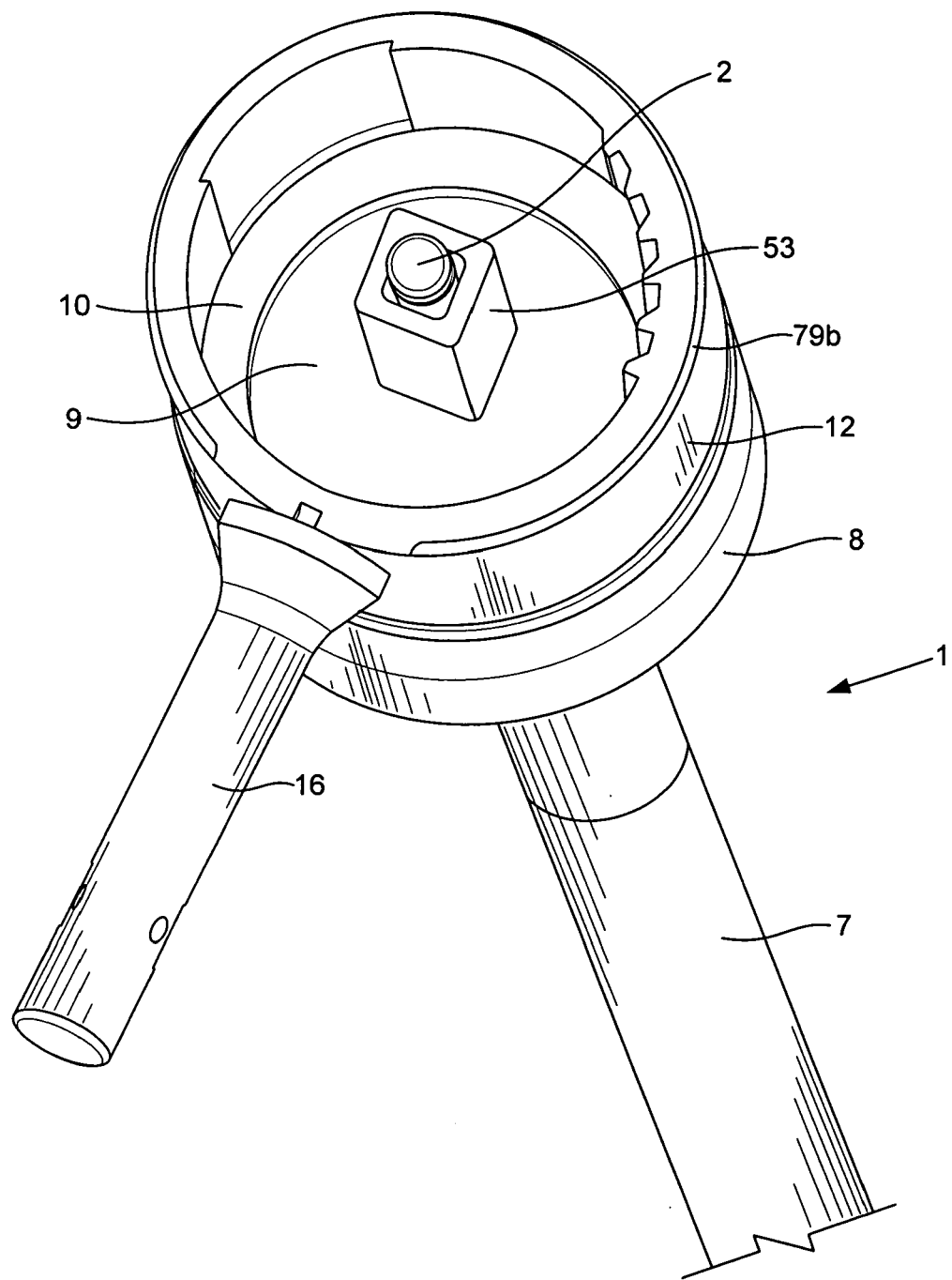
FIG. 15(B) illustrates a schematic diagram of an assembled ratcheting torque wrench with the ratchet cover, retaining ring, and ratchet gear removed according to an embodiment herein.
Figure 15C:
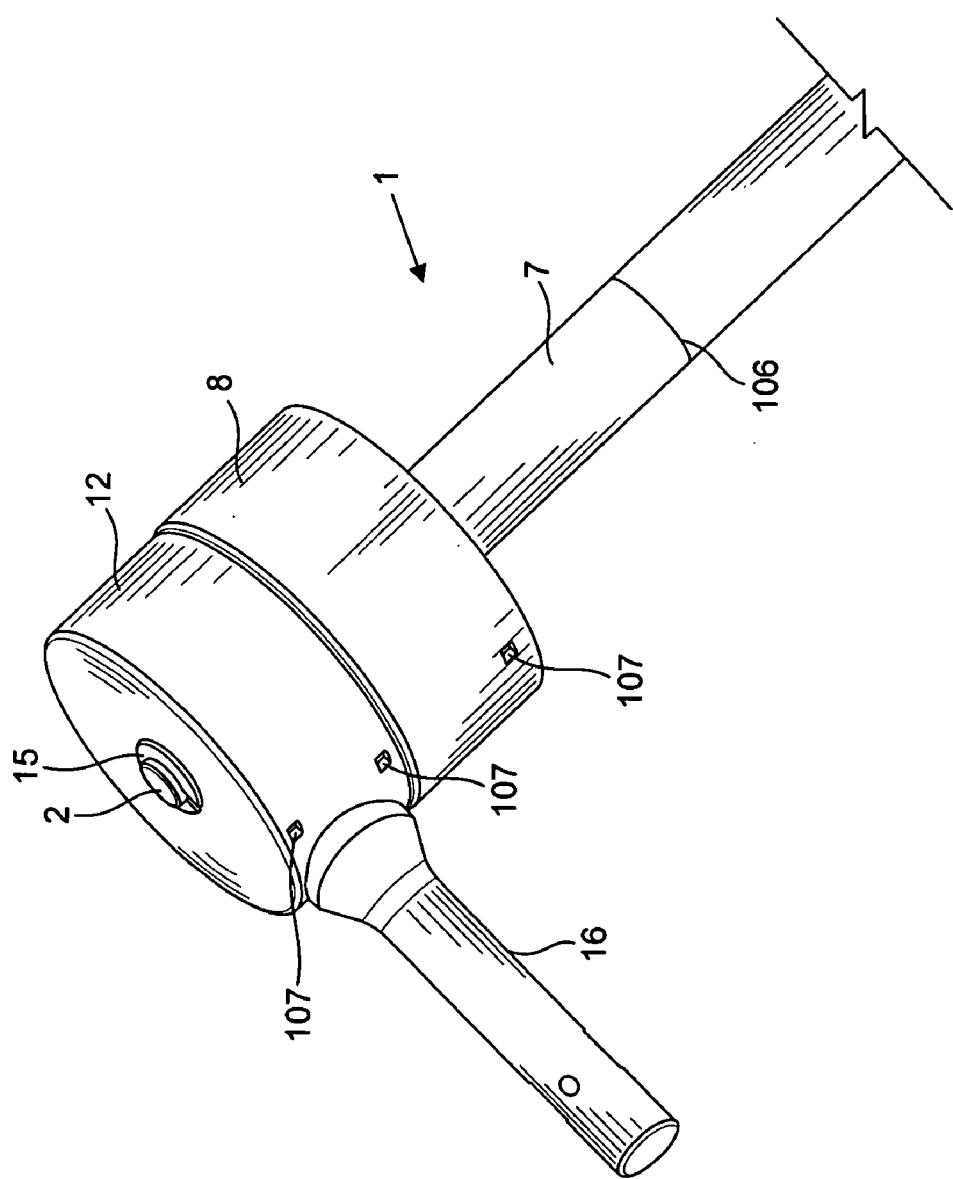
FIG. 15(C) illustrates a schematic diagram of an assembled ratcheting torque wrench according to an embodiment herein.

For clarity, FIG. 15(A) illustrates a schematic diagram of the ratcheting torque wrench 1 with the ratchet cover 14 and retaining ring 15 removed and FIG. 15(B) illustrates a schematic diagram of the ratcheting torque wrench 1 with the ratchet cover 14, retaining ring 15, and ratchet gear 11 removed. FIG. 15(C) illustrates a schematic diagram of an assembled ratcheting torque wrench 1.

Figure 16:
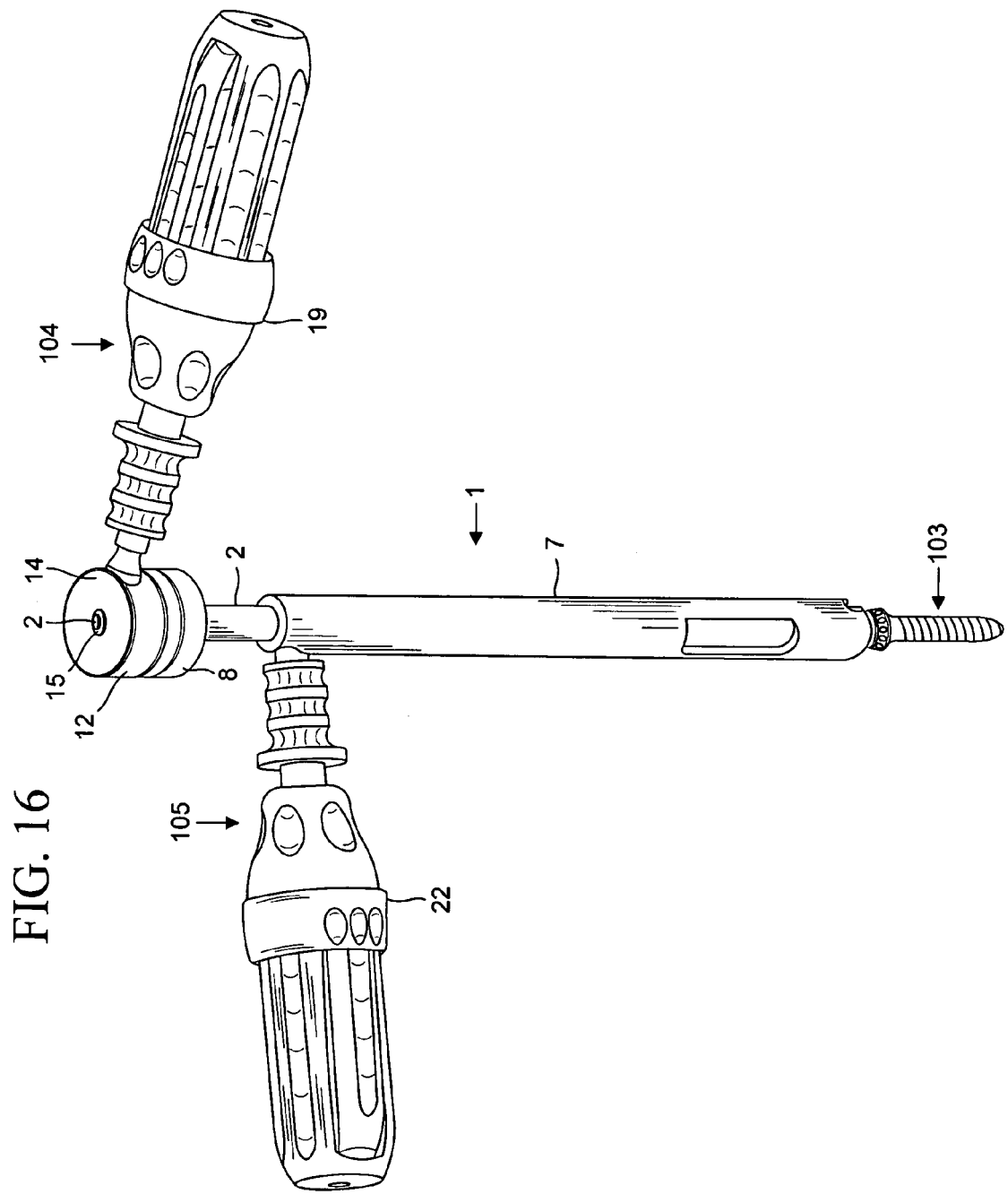
FIG. 16 illustrates a schematic diagram of a ratcheting torque wrench in use according to an embodiment herein.
Figure 17A:
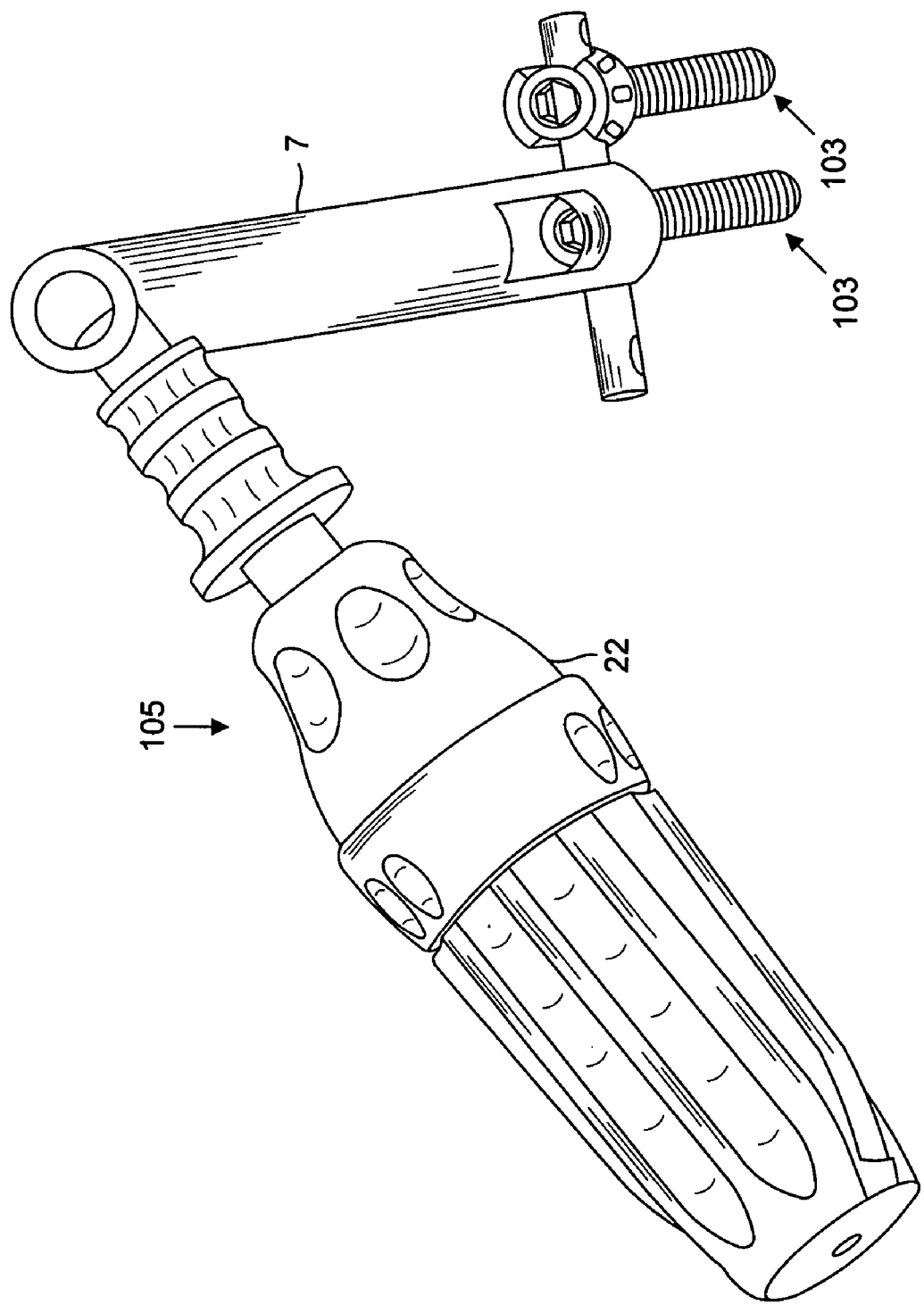
FIGS. 17(A) through 17(C) illustrate schematic diagrams of successive steps of using the ratcheting torque wrench of FIG. 16 according to an embodiment herein.
Figure 17B:
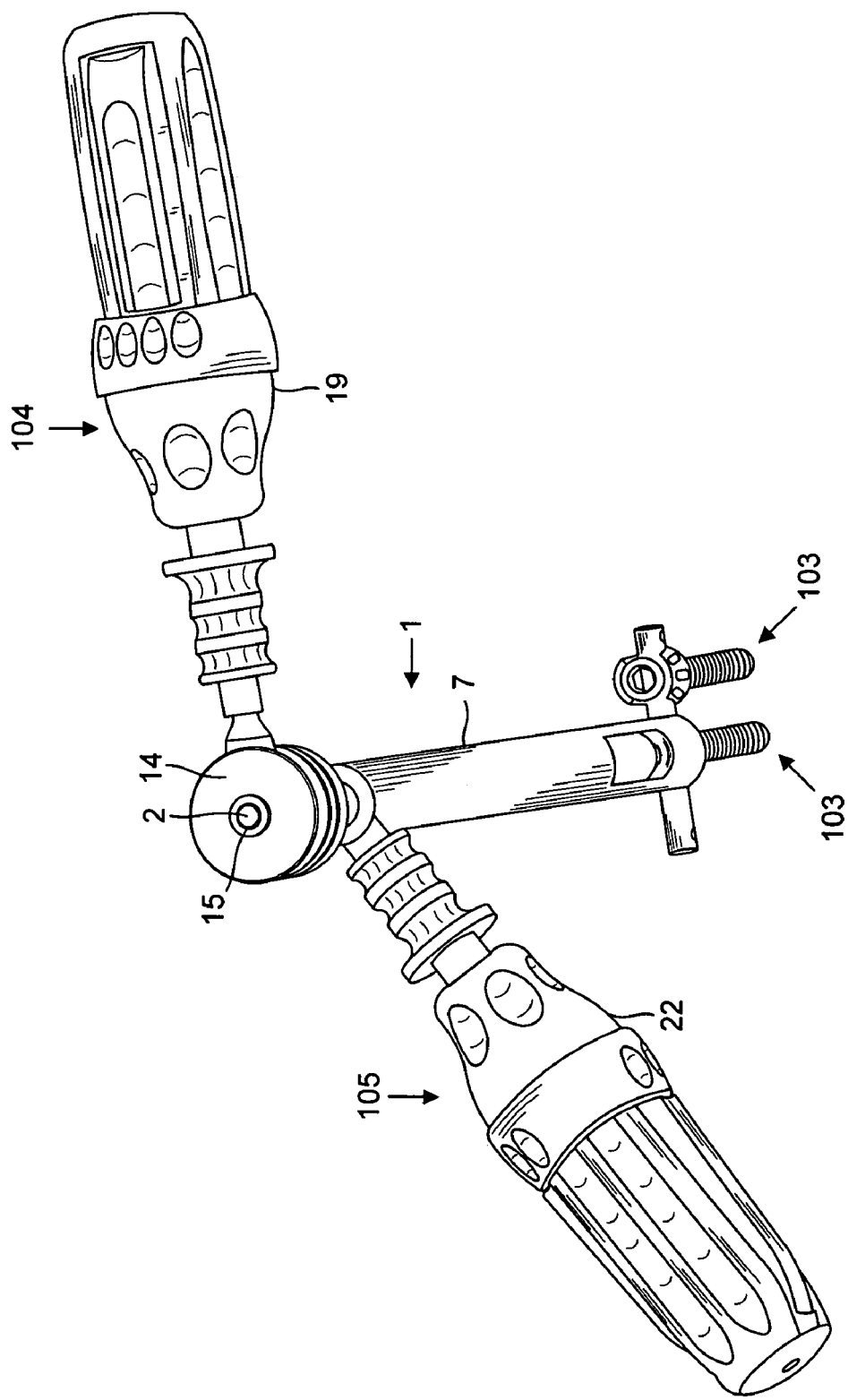
Figure 17C:
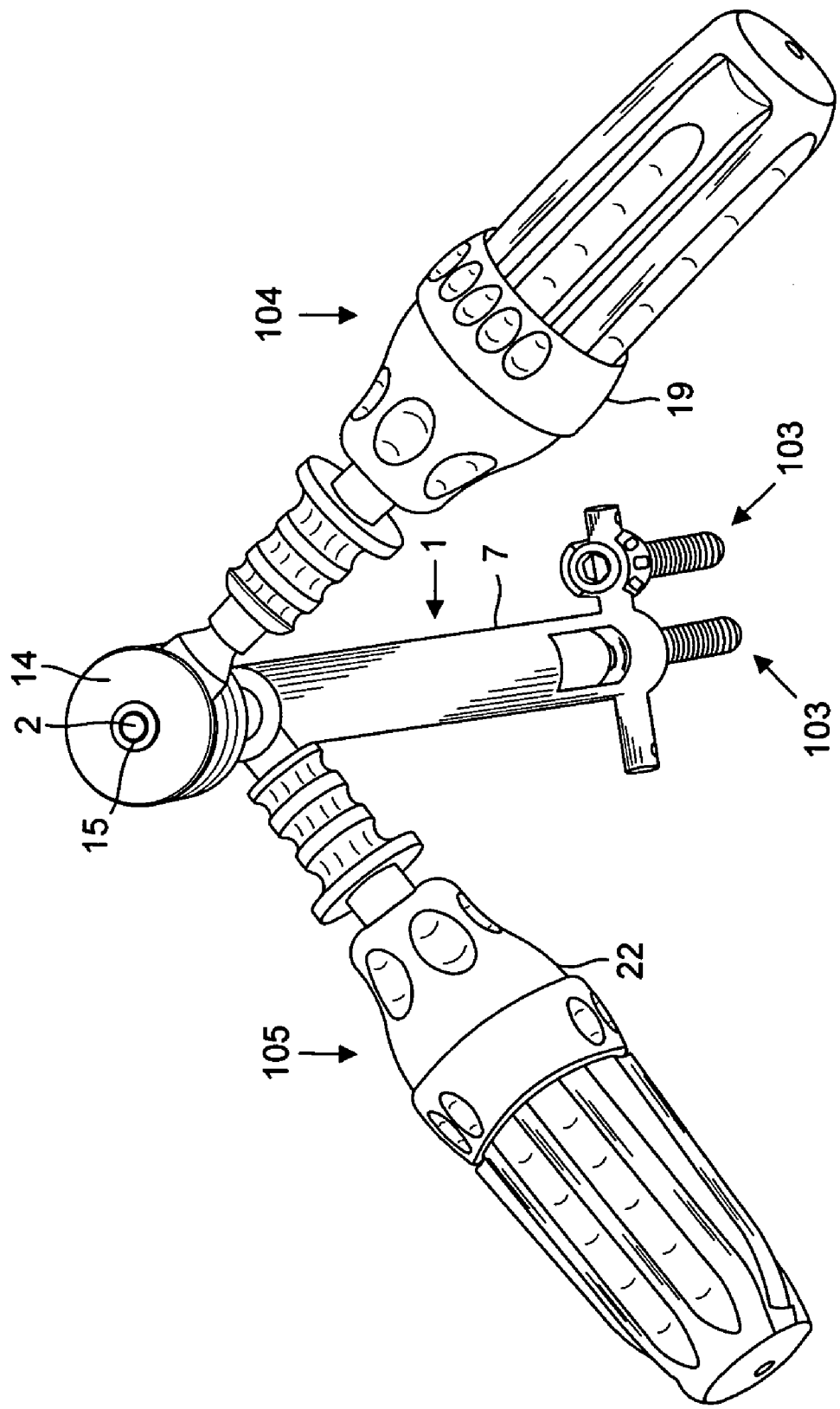
Figure 18:
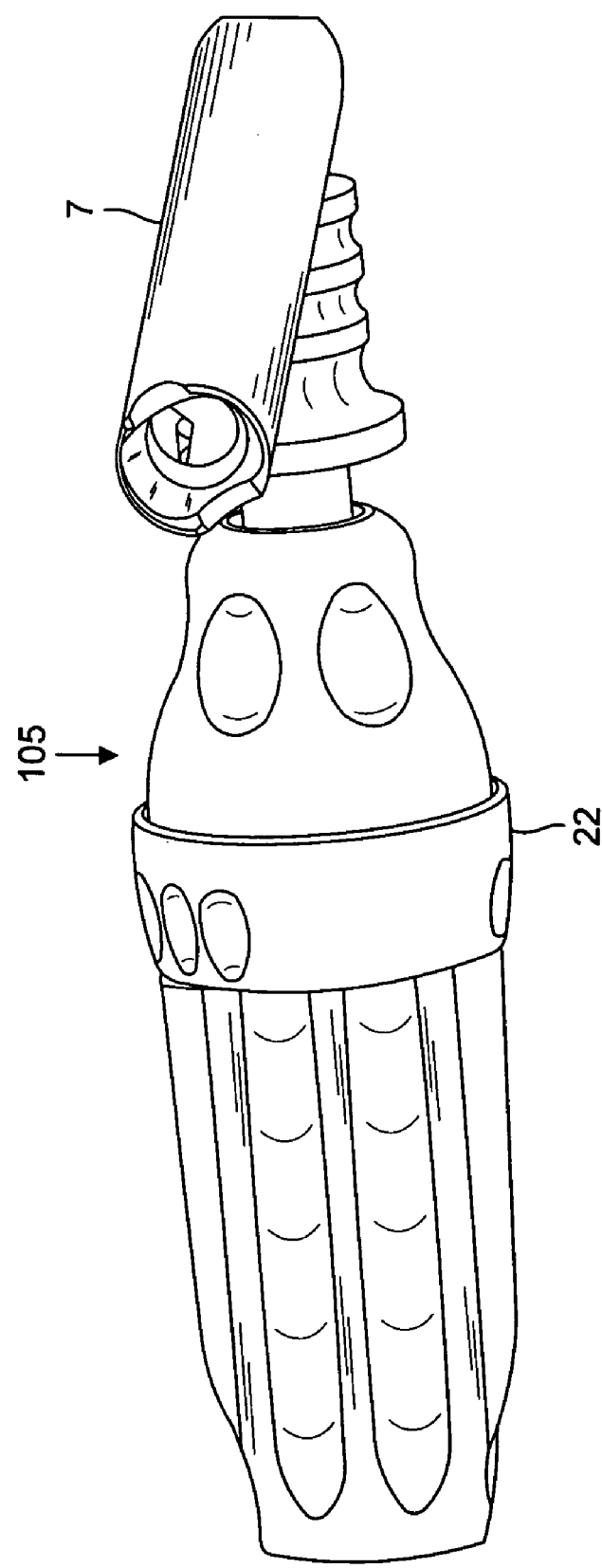
FIG. 18 illustrates an isolated view of the counter-torque wrench of FIG. 16 according to an embodiment herein.

FIGS. 16 through 17(C) illustrate schematic diagrams of the ratcheting torque wrench 1 in use (i.e., using a torque position wrench 104 and counter-torque position wrench 105 for engaging a pedicle bonescrew assembly 103, such as the pedicle bonescrew assembly disclosed in U.S. patent application Ser. No. 11/045,908, filed on Jan. 28, 2005 and entitled "Polyaxial Pedicle Screw Assembly", the complete disclosure of which, in its entirety, is herein incorporated by reference) according to an embodiment herein. FIGS. 17(A) through 17(C) illustrate schematic diagrams of successive steps of using the ratcheting torque wrench 1 of FIG. 16 according to an embodiment herein. In FIG. 17(A), only the sleeve 7 of the wrench 1 is shown for clarity with the handle 22 shown attached to the sleeve 7. Both the torque and counter-torque wrenches 104, 105, respectively, are shown in FIGS. 17(B) and 17(C). FIG. 18 illustrates an isolated view of the counter-torque wrench 105 using of FIG. 16 according to an embodiment herein.

With reference to FIGS. 1(A) through 18, the embodiments herein are preferably used to conduct the final locking or tightening of a locking element in an orthopedic implant. The embodiments function as follows. First, a counter-torque wrench 105 is configured by attaching handle 22 to the wrench 1 over a bone anchor and rod assembly 103. Next, a torque wrench 104 is configured by attaching handle 19 to the wrench 1. To ensure proper engagement between the torque wrench 104 and blocker (not shown) of a bone screw assembly 103, the groove 106 of sleeve 7 (best seen in FIGS. 1(A) and 3(A)) at the top of the torque wrench 104 is lined up with the top edge of the counter-torque wrench 105. Then, using the ratcheting mechanism 1 in the torque wrench 104, the torque wrench 104 can be rotated counter-clockwise to achieve the optimal position for leverage. Thereafter, the torque wrench 104 is rotated clockwise while the counter-torque wrench 105 is held firmly in place. Moreover, four laser marked indicators 107 (best seen in FIG. 15(C)) on the torque wrench 104 are present on the sleeve dial 8 and ratchet housing 12 to indicate the optimum tightening torque.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the appended claims.

What is claimed is:

1. A ratcheting torque wrench comprising:
 a shaft;
 a tip operatively connected to said shaft;
 a sleeve connected to said shaft;
 a sleeve dial connected to said sleeve;
 a ratchet housing positioned around said shaft;
 a ring connected to said ratchet housing;
 a ratchet gear connected to said ratchet housing;
 a spring connected to said ratchet housing and said ratchet gear;
 a retaining ring connected to said shaft; and
 a ratchet fitting connected to said ratchet housing.

2. The ratcheting torque wrench of claim 1, wherein said shaft comprises a torsional shaft having a first end and a second end distally located from the first end.

3. The ratcheting torque wrench of claim 2, further comprising a dowel pin dimensioned and configured to connect said tip to said first end of said torsional shaft.

4. The ratcheting torque wrench of claim 2, further comprising a ratchet cover dimensioned and configured to fit over said ratchet housing.

5. The ratcheting torque wrench of claim 4, wherein said retaining ring is connected to said ratchet cover, and wherein said retaining ring is dimensioned and configured to engage said second end of said torsional shaft.

6. The ratcheting torque wrench of claim 1, wherein said tip comprises a hex tip.

7. The ratcheting torque wrench of claim 1, wherein said sleeve is dimensioned and configured to fit over said torsional shaft.

8. The ratcheting torque wrench of claim 1, wherein said sleeve dial comprises a centrally located hole, wherein said sleeve dial is dimensioned and configured to fit around the sleeve such that the diameter of the sleeve dial hole is dimensioned and configured to accommodate said sleeve.

9. The ratcheting torque wrench of claim 1, wherein said ring comprises a nylon ring.

10. The ratcheting torque wrench of claim 1, wherein said ratchet gear comprises teeth dimensioned and configured around an outer perimeter of said ratchet gear.

11. The ratcheting torque wrench of claim 10, wherein said ratchet housing is dimensioned and configured to mate with said teeth of said ratchet gear.

12. The ratcheting torque wrench of claim 1, wherein said ratchet housing comprises a hole located through a wall of said ratchet housing.

13. The ratcheting torque wrench of claim 12, wherein said ratchet fitting engages said hole of said ratchet housing.

14. The ratcheting torque wrench of claim 1, wherein said ratchet fitting is dimensioned and configured to accommodate a first handle.

15. The ratcheting torque wrench of claim 1, wherein said sleeve comprises a hole to accommodate a second handle.

16. A ratcheting torque wrench comprising:
 a torsional shaft having a first end and a second end distally located from the first end;
 a hex tip;
 a dowel pin dimensioned and configured to connect said hex tip to said first end of said torsional shaft;
 a sleeve dimensioned and configured to fit over said torsional shaft;
 a sleeve dial having a centrally located hole, wherein said sleeve dial is dimensioned and configured to fit around the sleeve such that the diameter of the sleeve dial hole is dimensioned and configured to accommodate said sleeve;
 a shaft dial connected to said sleeve dial;
 a ratchet housing positioned around said shaft;
 a nylon ring connected to said ratchet housing;
 a ratchet gear connected to said ratchet housing, wherein said ratchet gear comprises teeth dimensioned and configured around an outer perimeter of said ratchet gear, wherein said ratchet housing is dimensioned and configured to mate with said teeth of said ratchet gear, wherein said ratchet housing comprises a hole located through a wall of said ratchet housing;

a shim connected to said ratchet housing and said ratchet gear;

a ratchet cover dimensioned and configured to fit over said ratchet housing;

a retaining ring connected to said ratchet cover and dimensioned and configured to engage said second end of said torsional shaft; and a ratchet fitting connected to said hole of said ratchet housing, wherein said ratchet fitting is dimensioned and configured to accommodate a first handle, wherein said sleeve comprises a hole to accommodate a second handle.

* * * * *